US008563270B2

(12) United States Patent
Inouye et al.

(10) Patent No.: US 8,563,270 B2
(45) Date of Patent: Oct. 22, 2013

(54) CALCIUM-BINDING PHOTOPROTEIN, GENE ENCODING THE SAME, AND USE THEREOF

(75) Inventors: Satoshi Inouye, Yokohama (JP); Yuiko Sahara, Yokohama (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 13/528,460

(22) Filed: Jun. 20, 2012

(65) Prior Publication Data

US 2012/0258486 A1 Oct. 11, 2012

Related U.S. Application Data

(62) Division of application No. 12/645,226, filed on Dec. 22, 2009, now Pat. No. 8,236,526, which is a division of application No. 11/826,915, filed on Jul. 19, 2007, now Pat. No. 7,666,980.

(60) Provisional application No. 60/831,939, filed on Jul. 20, 2006.

(51) Int. Cl.
*C12P 21/06* (2006.01)

(52) U.S. Cl.
USPC ......................................................... 435/69.1

(58) Field of Classification Search
USPC ......................................................... 435/69.1
See application file for complete search history.

(56) References Cited

U.S. PATENT DOCUMENTS

| | | | |
|---|---|---|---|
| 7,666,980 B2 * | 2/2010 | Inouye et al. | 530/300 |
| 8,236,526 B2 * | 8/2012 | Inouye et al. | 435/69.1 |
| 2005/0054838 A1 | 3/2005 | Otsuka et al. | |
| 2005/0130262 A1 | 6/2005 | Lambolez et al. | |
| 2007/0275377 A1 | 11/2007 | Golz et al. | |

FOREIGN PATENT DOCUMENTS

| | | |
|---|---|---|
| EP | 1413584 A1 | 4/2004 |
| GB | 2425535 A | 11/2006 |
| GB | 2426761 A | 12/2006 |
| WO | 030006497 A2 | 1/2003 |
| WO | 2005035559 A1 | 4/2005 |
| WO | 2006094805 A1 | 9/2006 |
| WO | 2007080622 A2 | 7/2007 |

OTHER PUBLICATIONS

Notice of Reasons for Rejection issued for JP2007-181675 [corresponding foreign application] on Apr. 24, 2012, and English translation thereof.
Search Report issued for GB0714037.9 [corresponding foreign application] on Nov. 6, 2007.
Office Action issued for GB0714037.9 [corresponding foreign application] on Jun. 28, 2010.
Office Action issued for U.S. Appl. No. 11/826,915 [parent application] on Jan. 28, 2009.
Office Action issued for U.S. Appl. No. 11/826,915 [parent application] on Apr. 20, 2009.
Prasher, D. et al., 1987, Sequence comparisons of complementary DNAs encoding aequorin isotypes, Biochemistry, V. 26, 1326-1332.
Head, JF et al., 2000, The crystal structure of the photoprotein aequorin at 2.3 A resolution, Nature, V 405, pp. 372-376, May.
Inouye, S et al, 1985, Cloning and sequence analysis of cDNA for the luminescent protein Aequorin, Proc. Natl. Acad. Sci. USA, V 82, pp. 3154-3158, May.
Inouye, S et al., 1993, Cloning and sequence analysis of cDNA for the Ca2+-activated photoprotein, Clytin, FEBS, V 315, No. 3, pp. 343-346, Janaury.
Office Action from GB patent office concering application GB0714037.9 [corresponding foreign application] issued Oct. 22, 2010.
Decision of Refusal issued on Mar. 5, 2013 for corresponding Japanese Patent Application No. 2007-181675.
English Translation of Decision of Refusal issued on Mar. 5, 2013 for corresponding Japanese Patent Application No. 2007-181675.
Watnick, et al., "Mutation Detection of PKD1 Identifies a Novel Mutation Common to Three Families with Aneurysms and/or Very-Early-Onset Disease," (1999) Am. J. Hum. Genet. 65: pp. 1561-1571.
Hardy, et al., "Characterization of Two Highly Conserved but Non-Allelic Cellular Disintegrins from Rabbit Testis," (1998) Gene, 206: pp. 127-135.

* cited by examiner

*Primary Examiner* — Karen Cochrane Carlson
(74) *Attorney, Agent, or Firm* — Hogan Lovells US LLP

(57) ABSTRACT

A protein according to the invention can be used to detect or measure calcium ions is provided. Further the protein is useful as a reporter protein or a luminescence marker. A polynucleotide according to the invention is also useful as a reporter gene.

5 Claims, 9 Drawing Sheets

FIG. 2

```
                                                                             -1
    a:pCL11                                              /ATQSKFQNFNMADTASKYA
    b:pCL41                                              /STF.....F..........
    c:pCL51R                                             /......S............
    d:pCL81                                              /......S............
                                                         _*************_*____ e:pCL21
    f:pCL31                              /NRLLSMSALAARSRLQRTANFHTSILLATDSKYA
    g:pCL61R          /KKGQEIKMLWFT...............................

+ + ++ ++ +                                                    66
a:VKLRPNFDNPKWVNRHKFMFNFLDINGDGKITLDEIVSKASDDICAKLGATPEQTKRHQDAVEAFF
b:................................................................
c:................................................................
d:................................................................
  ___*_*_*_____*_____*_____*_____*____
e:                                                       /RHQDAVEAFF
f:VKLDPDFANPKWINRHKFMFNFLDINGNGKITLDEIVSKASDDICAKLDATPEQTK.....V....
g:..............................................................I....

+ + ++ ++ +                                               132
a:KKIGMDYGKEVEFPAFVDGWKELANHDLKLWSQNKKSLIRDWGEAVFDIFDKDGSGSISLDEWKAY
b:.....................Y..........................................
c:.....................Y..........................................
d:.....................H..........................................
  __*_____*__*_**__*___**__*_____**___*__*_____*_____
e:KKMGMDYGKEVAFPEFIKGWEELAEHDLELWSQNKSTLIREWGDAVFDIFDKDASGSISLDEWKAY
f:...........A.........E............................................
g:...........P.........K............................................

+ + ++ ++ +                                              189
a:GRISGICSSDEDAEKTFKHCDLDNSGKLDVDEMTRQHLGFWYALDPNADGLYGNFVP
b:............................................T...........
c:............................................T...........
d:............................................T...........
  _____*_____*___**_____
e:GRISGICPSDEDAEKTFKHCDLDNSGKLDVDEMTRQHLGFWYTLDPTSDGLYGNFVP
f:.........................................................
g:.........................................................
```

FIG. 3
(a)
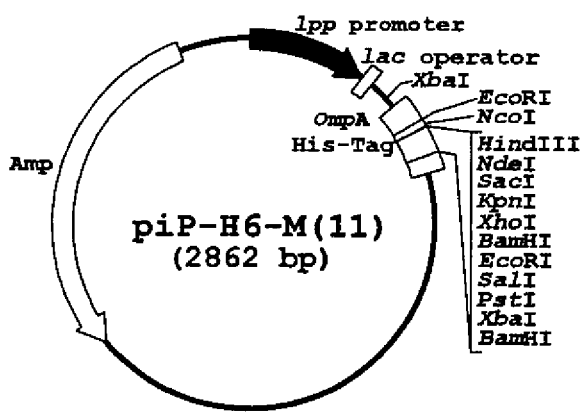
(b)
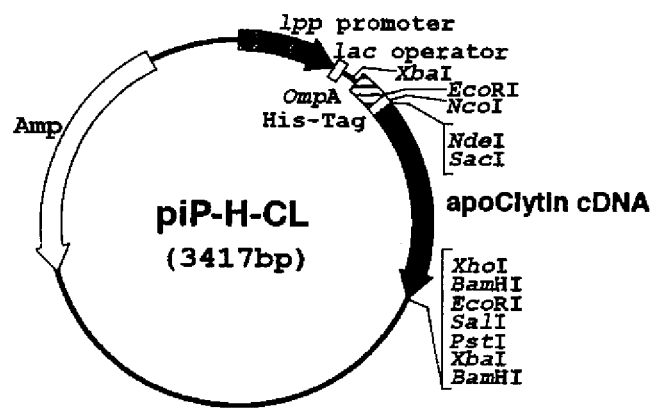
| OmpA signal peptide | His-tag | apoClytin cDNA |
|---|---|---|
| MKKTAIAIAVALAGFATVAQA | ANSHHHHHHGKLHMEL | RPNFD.......GNFVP* |
| | | Clytin-I cDNA(4-189) |
| MKKTAIAIAVALAGFATVAQA | ANSHHHHHHGKLHMEL | DPDFA.......GNFVP* |
| | | Clytin-II cDNA(4-189) |

SEQUENCE LISTING

<160> NUMBER OF SEQ ID NOS: 38

<210> SEQ ID NO 1
<211> LENGTH: 186
<212> TYPE: PRT
<213> ORGANISM: Clytia gregarium

<400> SEQUENCE: 1

```
Asp Pro Asp Phe Ala Asn Pro Lys Trp Ile Asn Arg His Lys Phe Met
1               5                   10                  15

Phe Asn Phe Leu Asp Ile Asn Gly Asn Gly Lys Ile Thr Leu Asp Glu
            20                  25                  30

Ile Val Ser Lys Ala Ser Asp Asp Ile Cys Ala Lys Leu Asp Ala Thr
        35                  40                  45

Pro Glu Gln Thr Lys Arg His Gln Asp Ala Val Glu Ala Phe Phe Lys
    50                  55                  60

Lys Met Gly Met Asp Tyr Gly Lys Glu Val Ala Phe Pro Glu Phe Ile
65                  70                  75                  80

Lys Gly Trp Glu Glu Leu Ala Glu His Asp Leu Glu Leu Trp Ser Gln
                85                  90                  95

Asn Lys Ser Thr Leu Ile Arg Glu Trp Gly Asp Ala Val Phe Asp Ile
            100                 105                 110

Phe Asp Lys Asp Ala Ser Gly Ser Ile Ser Leu Asp Glu Trp Lys Ala
        115                 120                 125

Tyr Gly Arg Ile Ser Gly Ile Cys Pro Ser Asp Glu Asp Ala Glu Lys
    130                 135                 140

Thr Phe Lys His Cys Asp Leu Asp Asn Ser Gly Lys Leu Asp Val Asp
145                 150                 155                 160

Glu Met Thr Arg Gln His Leu Gly Phe Trp Tyr Thr Leu Asp Pro Thr
                165                 170                 175

Ser Asp Gly Leu Tyr Gly Asn Phe Val Pro
            180                 185
```

<210> SEQ ID NO 2
<211> LENGTH: 558
<212> TYPE: DNA
<213> ORGANISM: Clytia gregarium

<400> SEQUENCE: 2

```
gatcctgatt ttgcaaatcc aaaatggatc aacagacaca aatttatgtt caacttttg      60 gacataaacg gtaatgggaa aatcacatta gatgaaatcg tctccaaagc ttcagacgac     120
atttgtgcta aactggatgc aacaccagaa cagaccaaac gtcaccagga tgctgttgaa     180 gcgttttca agaaaatggg catggattat ggtaagaag ttgcattccc agaatttatt       240
aagggatggg aagagttggc cgaacacgac ttggaactct ggtctcaaaa caaaagtaca     300
ttgatccgtg aatggggaga tgctgttttc gacattttcg acaaagacgc aagtggctca     360
```

```
atcagtttag acgaatggaa ggcttacgga cgaatctctg gaatctgtcc atcagacgaa    420
gacgctgaga agacgttcaa acattgtgat ttggacaaca gtggcaaact tgatgttgat    480
gagatgacca ggcaacattt aggcttctgg tacacattgg atccaacttc tgatggtctt    540
tatggcaatt ttgttccc                                                  558
```

<210> SEQ ID NO 3
<211> LENGTH: 189
<212> TYPE: PRT
<213> ORGANISM: Clytia gregarium

<400> SEQUENCE: 3

```
Val Lys Leu Asp Pro Asp Phe Ala Asn Pro Lys Trp Ile Asn Arg His
1               5                   10                  15

Lys Phe Met Phe Asn Phe Leu Asp Ile Asn Gly Asn Gly Lys Ile Thr
            20                  25                  30

Leu Asp Glu Ile Val Ser Lys Ala Ser Asp Ile Cys Ala Lys Leu
        35                  40                  45

Asp Ala Thr Pro Glu Gln Thr Lys Arg His Gln Asp Ala Val Glu Ala
    50                  55                  60

Phe Phe Lys Lys Met Gly Met Asp Tyr Gly Lys Glu Val Ala Phe Pro
65                  70                  75                  80

Glu Phe Ile Lys Gly Trp Glu Glu Leu Ala Glu His Asp Leu Glu Leu
                85                  90                  95

Trp Ser Gln Asn Lys Ser Thr Leu Ile Arg Glu Trp Gly Asp Ala Val
            100                 105                 110

Phe Asp Ile Phe Asp Lys Asp Ala Ser Gly Ser Ile Ser Leu Asp Glu
        115                 120                 125

Trp Lys Ala Tyr Gly Arg Ile Ser Gly Ile Cys Pro Ser Asp Glu Asp
    130                 135                 140

Ala Glu Lys Thr Phe Lys His Cys Asp Leu Asp Asn Ser Gly Lys Leu
145                 150                 155                 160

Asp Val Asp Glu Met Thr Arg Gln His Leu Gly Phe Trp Tyr Thr Leu
                165                 170                 175

Asp Pro Thr Ser Asp Gly Leu Tyr Gly Asn Phe Val Pro
            180                 185
```

<210> SEQ ID NO 4
<211> LENGTH: 567
<212> TYPE: DNA
<213> ORGANISM: Clytia gregarium

<400> SEQUENCE: 4

```
gtcaaactcg atcctgattt tgcaaatcca aatggatca acagacacaa atttatgttc      60
aactttttgg acataaacgg taatgggaaa atcacattag atgaaatcgt ctccaaagct    120
tcagacgaca tttgtgctaa actggatgca acaccagaac agaccaaacg tcaccaggat    180
gctgttgaag cgttttttcaa gaaaatgggc atggattatg gtaaagaagt tgcattccca    240
gaatttatta agggatggga gagttggcc gaacacgact ggaactctg gtctcaaaac     300 aaaagtacat tgatccgtga atggggagat gctgttttcg acattttcga caaagacgca    360
agtggctcaa tcagtttaga cgaatggaag gcttacggac gaatctctgg aatctgtcca    420
tcagacgaag acgctgagaa gacgttcaaa cattgtgatt tggacaacag tggcaaactt    480
gatgttgatg agatgaccag gcaacattta ggcttctggt acacattgga tccaacttct    540
gatggtcttt atggcaattt tgttccc                                        567
```

<210> SEQ ID NO 5
<211> LENGTH: 223
<212> TYPE: PRT
<213> ORGANISM: Clytia gregarium

<400> SEQUENCE: 5

```
Asn Arg Leu Leu Ser Met Ser Ala Leu Ala Ala Arg Ser Arg Leu Gln
1               5                   10                  15

Arg Thr Ala Asn Phe His Thr Ser Ile Leu Leu Ala Thr Asp Ser Lys
            20                  25                  30

Tyr Ala Val Lys Leu Asp Pro Asp Phe Ala Asn Pro Lys Trp Ile Asn
        35                  40                  45

Arg His Lys Phe Met Phe Asn Phe Leu Asp Ile Asn Gly Asn Gly Lys
    50                  55                  60

Ile Thr Leu Asp Glu Ile Val Ser Lys Ala Ser Asp Asp Ile Cys Ala
65                  70                  75                  80

Lys Leu Asp Ala Thr Pro Glu Gln Thr Lys Arg His Gln Asp Ala Val
                85                  90                  95

Glu Ala Phe Phe Lys Lys Met Gly Met Asp Tyr Gly Lys Glu Val Ala
            100                 105                 110

Phe Pro Glu Phe Ile Lys Gly Trp Glu Glu Leu Ala Glu His Asp Leu
        115                 120                 125

Glu Leu Trp Ser Gln Asn Lys Ser Thr Leu Ile Arg Glu Trp Gly Asp
    130                 135                 140

Ala Val Phe Asp Ile Phe Asp Lys Asp Ala Ser Gly Ser Ile Ser Leu
145                 150                 155                 160

Asp Glu Trp Lys Ala Tyr Gly Arg Ile Ser Gly Ile Cys Pro Ser Asp
                165                 170                 175

Glu Asp Ala Glu Lys Thr Phe Lys His Cys Asp Leu Asp Asn Ser Gly
            180                 185                 190

Lys Leu Asp Val Asp Glu Met Thr Arg Gln His Leu Gly Phe Trp Tyr
        195                 200                 205

Thr Leu Asp Pro Thr Ser Asp Gly Leu Tyr Gly Asn Phe Val Pro
    210                 215                 220
```

<210> SEQ ID NO 6
<211> LENGTH: 669
<212> TYPE: DNA
<213> ORGANISM: Clytia gregarium
<220> FEATURE:
<221> NAME/KEY: CDS
<222> LOCATION: (1)..(669)

<400> SEQUENCE: 6

```
aat cgt ctt ctt tcc atg tcg gct tta gct gca aga tca aga ttg caa      48
Asn Arg Leu Leu Ser Met Ser Ala Leu Ala Ala Arg Ser Arg Leu Gln
1               5                   10                  15 cgc aca gca aat ttt cac acc agc ata ctg ttg gct aca gat tca aaa      96
Arg Thr Ala Asn Phe His Thr Ser Ile Leu Leu Ala Thr Asp Ser Lys
            20                  25                  30 tac gcg gtc aaa ctc gat cct gat ttt gca aat cca aaa tgg atc aac     144
Tyr Ala Val Lys Leu Asp Pro Asp Phe Ala Asn Pro Lys Trp Ile Asn
        35                  40                  45 aga cac aaa ttt atg ttc aac ttt ttg gac ata aac ggt aat ggg aaa     192
Arg His Lys Phe Met Phe Asn Phe Leu Asp Ile Asn Gly Asn Gly Lys
    50                  55                  60 atc aca tta gat gaa atc gtc tcc aaa gct tca gac gac att tgt gct     240
Ile Thr Leu Asp Glu Ile Val Ser Lys Ala Ser Asp Asp Ile Cys Ala
```

```
aaa ctg gat gca aca cca gaa cag acc aaa cgt cac cag gat gct gtt      288
Lys Leu Asp Ala Thr Pro Glu Gln Thr Lys Arg His Gln Asp Ala Val
                85                  90                  95 gaa gcg ttt ttc aag aaa atg ggc atg gat tat ggt aaa gaa gtt gca      336
Glu Ala Phe Phe Lys Lys Met Gly Met Asp Tyr Gly Lys Glu Val Ala
    100                 105                 110 ttc cca gaa ttt att aag gga tgg gaa gag ttg gcc gaa cac gac ttg      384
Phe Pro Glu Phe Ile Lys Gly Trp Glu Glu Leu Ala Glu His Asp Leu
        115                 120                 125 gaa ctc tgg tct caa aac aaa agt aca ttg atc cgt gaa tgg gga gat      432
Glu Leu Trp Ser Gln Asn Lys Ser Thr Leu Ile Arg Glu Trp Gly Asp
            130                 135                 140 gct gtt ttc gac att ttc gac aaa gac gca agt ggc tca atc agt tta      480
Ala Val Phe Asp Ile Phe Asp Lys Asp Ala Ser Gly Ser Ile Ser Leu
145                 150                 155                 160 gac gaa tgg aag gct tac gga cga atc tct gga atc tgt cca tca gac      528
Asp Glu Trp Lys Ala Tyr Gly Arg Ile Ser Gly Ile Cys Pro Ser Asp
                165                 170                 175 gaa gac gct gag aag acg ttc aaa cat tgt gat ttg gac aac agt ggc      576
Glu Asp Ala Glu Lys Thr Phe Lys His Cys Asp Leu Asp Asn Ser Gly
    180                 185                 190 aaa ctt gat gtt gat gag atg acc agg caa cat tta ggc ttc tgg tac      624
Lys Leu Asp Val Asp Glu Met Thr Arg Gln His Leu Gly Phe Trp Tyr
        195                 200                 205 aca ttg gat cca act tct gat ggt ctt tat ggc aat ttt gtt ccc          669
Thr Leu Asp Pro Thr Ser Asp Gly Leu Tyr Gly Asn Phe Val Pro
            210                 215                 220
```

<210> SEQ ID NO 7
<211> LENGTH: 235
<212> TYPE: PRT
<213> ORGANISM: Clytia gregarium

<400> SEQUENCE: 7

```
Lys Lys Gly Gln Glu Ile Lys Met Leu Trp Phe Thr Asn Arg Leu Leu
1               5                   10                  15

Ser Met Ser Ala Leu Ala Ala Arg Ser Arg Leu Gln Arg Thr Ala Asn
                20                  25                  30

Phe His Thr Ser Ile Leu Leu Ala Thr Asp Ser Lys Tyr Ala Val Lys
            35                  40                  45

Leu Asp Pro Asp Phe Ala Asn Pro Lys Trp Ile Asn Arg His Lys Phe
        50                  55                  60

Met Phe Asn Phe Leu Asp Ile Asn Gly Asn Gly Lys Ile Thr Leu Asp
65                  70                  75                  80

Glu Ile Val Ser Lys Ala Ser Asp Asp Ile Cys Ala Lys Leu Asp Ala
                85                  90                  95

Thr Pro Glu Gln Thr Lys Arg His Gln Asp Ala Ile Glu Ala Phe Phe
            100                 105                 110

Lys Lys Met Gly Met Asp Tyr Gly Lys Glu Val Pro Phe Pro Glu Phe
        115                 120                 125

Ile Lys Gly Trp Glu Glu Leu Ala Lys His Asp Leu Glu Leu Trp Ser
    130                 135                 140

Gln Asn Lys Ser Thr Leu Ile Arg Glu Trp Gly Asp Ala Val Phe Asp
145                 150                 155                 160

Ile Phe Asp Lys Asp Ala Ser Gly Ser Ile Ser Leu Asp Glu Trp Lys
                165                 170                 175

Ala Tyr Gly Arg Ile Ser Gly Ile Cys Pro Ser Asp Glu Asp Ala Glu
```

|  |  |  |  |  | 180 |  |  |  |  | 185 |  |  |  |  | 190 |  |
|---|---|---|---|---|---|---|---|---|---|---|---|---|---|---|---|---|

Lys Thr Phe Lys His Cys Asp Leu Asp Asn Ser Gly Lys Leu Asp Val
        195                 200                 205

Asp Glu Met Thr Arg Gln His Leu Gly Phe Trp Tyr Thr Leu Asp Pro
    210                 215                 220

Thr Ser Asp Gly Leu Tyr Gly Asn Phe Val Pro
225               230                 235

<210> SEQ ID NO 8
<211> LENGTH: 705
<212> TYPE: DNA
<213> ORGANISM: Clytia gregarium
<220> FEATURE:
<221> NAME/KEY: CDS
<222> LOCATION: (1)..(705)

<400> SEQUENCE: 8

| aaa aaa gga caa gaa atc aag atg ctt tgg ttt aca aat cgt ctt ctt | 48 |
|---|---|
| Lys Lys Gly Gln Glu Ile Lys Met Leu Trp Phe Thr Asn Arg Leu Leu | |
| 1                  5                    10                15 | |

| tcc atg tca gct tta gct gca aga tca aga tta caa cgc aca gca aat | 96 |
|---|---|
| Ser Met Ser Ala Leu Ala Ala Arg Ser Arg Leu Gln Arg Thr Ala Asn | |
|                20                    25                    30 | |

| ttt cac acc agc ata ctg ttg gct aca gat tca aaa tac gca gtc aaa | 144 |
|---|---|
| Phe His Thr Ser Ile Leu Leu Ala Thr Asp Ser Lys Tyr Ala Val Lys | |
|           35                    40                    45 | |

| ctc gat cct gat ttc gca aat cca aaa tgg atc aac aga cac aaa ttt | 192 |
|---|---|
| Leu Asp Pro Asp Phe Ala Asn Pro Lys Trp Ile Asn Arg His Lys Phe | |
| 50                 55                    60 | |

| atg ttc aac ttt ttg gac ata aac ggt aat ggg aaa atc aca tta gat | 240 |
|---|---|
| Met Phe Asn Phe Leu Asp Ile Asn Gly Asn Gly Lys Ile Thr Leu Asp | |
| 65                 70                   75                80 | |

| gaa atc gtc tcc aaa gct tca gac gac att tgt gct aaa ctg gat gca | 288 |
|---|---|
| Glu Ile Val Ser Lys Ala Ser Asp Asp Ile Cys Ala Lys Leu Asp Ala | |
|                    85                    90                95 | |

| aca cca gaa cag acc aaa cgt cac cag gat gct att gaa gcc ttt ttc | 336 |
|---|---|
| Thr Pro Glu Gln Thr Lys Arg His Gln Asp Ala Ile Glu Ala Phe Phe | |
|                100                  105               110 | |

| aag aaa atg ggc atg gat tat ggt aaa gaa gtt cca ttc cca gaa ttt | 384 |
|---|---|
| Lys Lys Met Gly Met Asp Tyr Gly Lys Glu Val Pro Phe Pro Glu Phe | |
|           115                  120               125 | |

| att aag gga tgg gaa gag ttg gcc aaa cac gac ttg gaa ctc tgg tct | 432 |
|---|---|
| Ile Lys Gly Trp Glu Glu Leu Ala Lys His Asp Leu Glu Leu Trp Ser | |
|         130                  135               140 | |

| caa aac aaa agt aca ttg atc cgt gaa tgg gga gat gct gtt ttc gac | 480 |
|---|---|
| Gln Asn Lys Ser Thr Leu Ile Arg Glu Trp Gly Asp Ala Val Phe Asp | |
| 145                150                  155               160 | |

| att ttc gac aaa gac gca agt ggc tca atc agt tta gac gaa tgg aag | 528 |
|---|---|
| Ile Phe Asp Lys Asp Ala Ser Gly Ser Ile Ser Leu Asp Glu Trp Lys | |
|                165                  170               175 | |

| gct tac gga cga atc tct gga atc tgt cca tct gac gaa gac gct gag | 576 |
|---|---|
| Ala Tyr Gly Arg Ile Ser Gly Ile Cys Pro Ser Asp Glu Asp Ala Glu | |
|                   180                  185               190 | |

| aag acg ttc aaa cat tgc gat ttg gac aac agt ggc aaa ctt gat gtt | 624 |
|---|---|
| Lys Thr Phe Lys His Cys Asp Leu Asp Asn Ser Gly Lys Leu Asp Val | |
|           195                  200               205 | |

| gat gag atg act agg caa cat tta ggc ttc tgg tac aca ttg gat cca | 672 |
|---|---|
| Asp Glu Met Thr Arg Gln His Leu Gly Phe Trp Tyr Thr Leu Asp Pro | |
|         210                  215               220 | |

| act tct gat ggt ctt tat ggc aat ttt gtt ccc | 705 |
|---|---|
| Thr Ser Asp Gly Leu Tyr Gly Asn Phe Val Pro | |

<210> SEQ ID NO 9
<211> LENGTH: 189
<212> TYPE: PRT
<213> ORGANISM: Clytia gregarium

<400> SEQUENCE: 9

```
Val Lys Leu Asp Pro Asp Phe Ala Asn Pro Lys Trp Ile Asn Arg His
 1               5                  10                  15
Lys Phe Met Phe Asn Phe Leu Asp Ile Asn Gly Asn Gly Lys Ile Thr
             20                  25                  30
Leu Asp Glu Ile Val Ser Lys Ala Ser Asp Asp Ile Cys Ala Lys Leu
         35                  40                  45
Asp Ala Thr Pro Glu Gln Thr Lys Arg His Gln Asp Ala Ile Glu Ala
     50                  55                  60
Phe Phe Lys Lys Met Gly Met Asp Tyr Gly Lys Glu Val Pro Phe Pro
 65                  70                  75                  80
Glu Phe Ile Lys Gly Trp Glu Glu Leu Ala Lys His Asp Leu Glu Leu
                 85                  90                  95
Trp Ser Gln Asn Lys Ser Thr Leu Ile Arg Glu Trp Gly Asp Ala Val
            100                 105                 110
Phe Asp Ile Phe Asp Lys Asp Ala Ser Gly Ser Ile Ser Leu Asp Glu
        115                 120                 125
Trp Lys Ala Tyr Gly Arg Ile Ser Gly Ile Cys Pro Ser Asp Glu Asp
    130                 135                 140
Ala Glu Lys Thr Phe Lys His Cys Asp Leu Asp Asn Ser Gly Lys Leu
145                 150                 155                 160
Asp Val Asp Glu Met Thr Arg Gln His Leu Gly Phe Trp Tyr Thr Leu
                165                 170                 175
Asp Pro Thr Ser Asp Gly Leu Tyr Gly Asn Phe Val Pro
            180                 185
```

<210> SEQ ID NO 10
<211> LENGTH: 567
<212> TYPE: DNA
<213> ORGANISM: Clytia gregarium
<220> FEATURE:
<221> NAME/KEY: CDS
<222> LOCATION: (1)..(567)

<400> SEQUENCE: 10

```
gtc aaa ctc gat cct gat ttc gca aat cca aaa tgg atc aac aga cac      48
Val Lys Leu Asp Pro Asp Phe Ala Asn Pro Lys Trp Ile Asn Arg His
 1               5                  10                  15 aaa ttt atg ttc aac ttt ttg gac ata aac ggt aat ggg aaa atc aca      96
Lys Phe Met Phe Asn Phe Leu Asp Ile Asn Gly Asn Gly Lys Ile Thr
             20                  25                  30 tta gat gaa atc gtc tcc aaa gct tca gac gac att tgt gct aaa ctg     144
Leu Asp Glu Ile Val Ser Lys Ala Ser Asp Asp Ile Cys Ala Lys Leu
         35                  40                  45 gat gca aca cca gaa cag acc aaa cgt cac cag gat gct att gaa gcc     192
Asp Ala Thr Pro Glu Gln Thr Lys Arg His Gln Asp Ala Ile Glu Ala
     50                  55                  60 ttt ttc aag aaa atg ggc atg gat tat ggt aaa gaa gtt cca ttc cca     240
Phe Phe Lys Lys Met Gly Met Asp Tyr Gly Lys Glu Val Pro Phe Pro
 65                  70                  75                  80 gaa ttt att aag gga tgg gaa gag ttg gcc aaa cac gac ttg gaa ctc     288
Glu Phe Ile Lys Gly Trp Glu Glu Leu Ala Lys His Asp Leu Glu Leu
                 85                  90                  95
```

```
tgg tct caa aac aaa agt aca ttg atc cgt gaa tgg gga gat gct gtt      336
Trp Ser Gln Asn Lys Ser Thr Leu Ile Arg Glu Trp Gly Asp Ala Val
            100                 105                 110 ttc gac att ttc gac aaa gac gca agt ggc tca atc agt tta gac gaa      384
Phe Asp Ile Phe Asp Lys Asp Ala Ser Gly Ser Ile Ser Leu Asp Glu
        115                 120                 125 tgg aag gct tac gga cga atc tct gga atc tgt cca tct gac gaa gac      432
Trp Lys Ala Tyr Gly Arg Ile Ser Gly Ile Cys Pro Ser Asp Glu Asp
130                 135                 140 gct gag aag acg ttc aaa cat tgc gat ttg gac aac agt ggc aaa ctt      480
Ala Glu Lys Thr Phe Lys His Cys Asp Leu Asp Asn Ser Gly Lys Leu
145                 150                 155                 160 gat gtt gat gag atg act agg caa cat tta ggc ttc tgg tac aca ttg      528
Asp Val Asp Glu Met Thr Arg Gln His Leu Gly Phe Trp Tyr Thr Leu
                165                 170                 175 gat cca act tct gat ggt ctt tat ggc aat ttt gtt ccc                  567
Asp Pro Thr Ser Asp Gly Leu Tyr Gly Asn Phe Val Pro
            180                 185
```

<210> SEQ ID NO 11
<211> LENGTH: 186
<212> TYPE: PRT
<213> ORGANISM: Clytia gregarium

<400> SEQUENCE: 11

```
Asp Pro Asp Phe Ala Asn Pro Lys Trp Ile Asn Arg His Lys Phe Met
1               5                   10                  15

Phe Asn Phe Leu Asp Ile Asn Gly Asn Gly Lys Ile Thr Leu Asp Glu
            20                  25                  30

Ile Val Ser Lys Ala Ser Asp Asp Ile Cys Ala Lys Leu Asp Ala Thr
        35                  40                  45

Pro Glu Gln Thr Lys Arg His Gln Asp Ala Ile Glu Ala Phe Phe Lys
    50                  55                  60

Lys Met Gly Met Asp Tyr Gly Lys Glu Val Pro Phe Pro Glu Phe Ile
65                  70                  75                  80

Lys Gly Trp Glu Glu Leu Ala Lys His Asp Leu Glu Leu Trp Ser Gln
                85                  90                  95

Asn Lys Ser Thr Leu Ile Arg Glu Trp Gly Asp Ala Val Phe Asp Ile
            100                 105                 110

Phe Asp Lys Asp Ala Ser Gly Ser Ile Ser Leu Asp Glu Trp Lys Ala
        115                 120                 125

Tyr Gly Arg Ile Ser Gly Ile Cys Pro Ser Asp Glu Asp Ala Glu Lys
    130                 135                 140

Thr Phe Lys His Cys Asp Leu Asp Asn Ser Gly Lys Leu Asp Val Asp
145                 150                 155                 160

Glu Met Thr Arg Gln His Leu Gly Phe Trp Tyr Thr Leu Asp Pro Thr
                165                 170                 175

Ser Asp Gly Leu Tyr Gly Asn Phe Val Pro
            180                 185
```

<210> SEQ ID NO 12
<211> LENGTH: 558
<212> TYPE: DNA
<213> ORGANISM: Clytia gregarium
<220> FEATURE:
<221> NAME/KEY: CDS
<222> LOCATION: (1)..(558)

<400> SEQUENCE: 12

```
gat cct gat ttc gca aat cca aaa tgg atc aac aga cac aaa ttt atg      48
Asp Pro Asp Phe Ala Asn Pro Lys Trp Ile Asn Arg His Lys Phe Met
1               5                   10                  15 ttc aac ttt ttg gac ata aac ggt aat ggg aaa atc aca tta gat gaa      96
Phe Asn Phe Leu Asp Ile Asn Gly Asn Gly Lys Ile Thr Leu Asp Glu
            20                  25                  30 atc gtc tcc aaa gct tca gac gac att tgt gct aaa ctg gat gca aca     144
Ile Val Ser Lys Ala Ser Asp Asp Ile Cys Ala Lys Leu Asp Ala Thr
        35                  40                  45 cca gaa cag acc aaa cgt cac cag gat gct att gaa gcc ttt ttc aag     192
Pro Glu Gln Thr Lys Arg His Gln Asp Ala Ile Glu Ala Phe Phe Lys
50                  55                  60 aaa atg ggc atg gat tat ggt aaa gaa gtt cca ttc cca gaa ttt att     240
Lys Met Gly Met Asp Tyr Gly Lys Glu Val Pro Phe Pro Glu Phe Ile
65              70                  75                  80 aag gga tgg gaa gag ttg gcc aaa cac gac ttg gaa ctc tgg tct caa     288
Lys Gly Trp Glu Glu Leu Ala Lys His Asp Leu Glu Leu Trp Ser Gln
                85                  90                  95 aac aaa agt aca ttg atc cgt gaa tgg gga gat gct gtt ttc gac att     336
Asn Lys Ser Thr Leu Ile Arg Glu Trp Gly Asp Ala Val Phe Asp Ile
            100                 105                 110 ttc gac aaa gac gca agt ggc tca atc agt tta gac gaa tgg aag gct     384
Phe Asp Lys Asp Ala Ser Gly Ser Ile Ser Leu Asp Glu Trp Lys Ala
        115                 120                 125 tac gga cga atc tct gga atc tgt cca tct gac gaa gac gct gag aag     432
Tyr Gly Arg Ile Ser Gly Ile Cys Pro Ser Asp Glu Asp Ala Glu Lys
130                 135                 140 acg ttc aaa cat tgc gat ttg gac aac agt ggc aaa ctt gat gtt gat     480
Thr Phe Lys His Cys Asp Leu Asp Asn Ser Gly Lys Leu Asp Val Asp
145                 150                 155                 160 gag atg act agg caa cat tta ggc ttc tgg tac aca ttg gat cca act     528
Glu Met Thr Arg Gln His Leu Gly Phe Trp Tyr Thr Leu Asp Pro Thr
                165                 170                 175 tct gat ggt ctt tat ggc aat ttt gtt ccc                             558
Ser Asp Gly Leu Tyr Gly Asn Phe Val Pro
            180                 185

<210> SEQ ID NO 13
<211> LENGTH: 133
<212> TYPE: PRT
<213> ORGANISM: Clytia gregarium

<400> SEQUENCE: 13

Arg His Gln Asp Ala Val Glu Ala Phe Phe Lys Lys Met Gly Met Asp
1               5                   10                  15

Tyr Gly Lys Glu Val Ala Phe Pro Glu Phe Ile Lys Gly Trp Glu Glu
            20                  25                  30

Leu Ala Glu His Asp Leu Glu Leu Trp Ser Gln Asn Lys Ser Thr Leu
        35                  40                  45

Ile Arg Glu Trp Gly Asp Ala Val Phe Asp Ile Phe Asp Lys Asp Ala
    50                  55                  60

Ser Gly Ser Ile Ser Leu Asp Glu Trp Lys Ala Tyr Gly Arg Ile Ser
65                  70                  75                  80

Gly Ile Cys Pro Ser Asp Glu Asp Ala Glu Lys Thr Phe Lys His Cys
                85                  90                  95

Asp Leu Asp Asn Ser Gly Lys Leu Asp Val Asp Glu Met Thr Arg Gln
            100                 105                 110

His Leu Gly Phe Trp Tyr Thr Leu Asp Pro Thr Ser Asp Gly Leu Tyr
        115                 120                 125
```

-continued

Gly Asn Phe Val Pro
    130

<210> SEQ ID NO 14
<211> LENGTH: 399
<212> TYPE: DNA
<213> ORGANISM: Clytia gregarium
<220> FEATURE:
<221> NAME/KEY: CDS
<222> LOCATION: (1)..(399)

<400> SEQUENCE: 14

```
cgt cac cag gat gct gtt gaa gcc ttt ttc aag aaa atg ggc atg gat        48
Arg His Gln Asp Ala Val Glu Ala Phe Phe Lys Lys Met Gly Met Asp
1               5                   10                  15 tat ggt aaa gaa gtt gca ttc cca gaa ttt att aag gga tgg gaa gag        96
Tyr Gly Lys Glu Val Ala Phe Pro Glu Phe Ile Lys Gly Trp Glu Glu
            20                  25                  30 ttg gcc gaa cac gac ttg gaa ctc tgg tct caa aac aaa agt aca ttg       144
Leu Ala Glu His Asp Leu Glu Leu Trp Ser Gln Asn Lys Ser Thr Leu
        35                  40                  45 atc cgt gaa tgg gga gat gct gtt ttc gac att ttc gac aaa gac gca       192
Ile Arg Glu Trp Gly Asp Ala Val Phe Asp Ile Phe Asp Lys Asp Ala
    50                  55                  60 agt ggc tca atc agt tta gac gaa tgg aag gct tac gga cga atc tct       240
Ser Gly Ser Ile Ser Leu Asp Glu Trp Lys Ala Tyr Gly Arg Ile Ser
65                  70                  75                  80 gga atc tgt cca tca gac gaa gac gct gag aag acg ttc aaa cat tgt       288
Gly Ile Cys Pro Ser Asp Glu Asp Ala Glu Lys Thr Phe Lys His Cys
                85                  90                  95 gat ttg gac aac agt ggc aaa ctt gat gtt gat gag atg acc agg caa       336
Asp Leu Asp Asn Ser Gly Lys Leu Asp Val Asp Glu Met Thr Arg Gln
            100                 105                 110 cat tta ggc ttc tgg tac aca ttg gat cca act tct gat ggt ctt tat       384
His Leu Gly Phe Trp Tyr Thr Leu Asp Pro Thr Ser Asp Gly Leu Tyr
        115                 120                 125 ggc aat ttt gtt ccc                                                    399
Gly Asn Phe Val Pro
    130
```

<210> SEQ ID NO 15
<211> LENGTH: 208
<212> TYPE: PRT
<213> ORGANISM: Clytia gregarium

<400> SEQUENCE: 15

Ala Thr Gln Ser Lys Phe Gln Asn Phe Asn Met Ala Asp Thr Ala Ser
1               5                   10                  15

Lys Tyr Ala Val Lys Leu Arg Pro Asn Phe Asp Asn Pro Lys Trp Val
            20                  25                  30

Asn Arg His Lys Phe Met Phe Asn Phe Leu Asp Ile Asn Gly Asp Gly
        35                  40                  45

Lys Ile Thr Leu Asp Glu Ile Val Ser Lys Ala Ser Asp Asp Ile Cys
    50                  55                  60

Ala Lys Leu Gly Ala Thr Pro Glu Gln Thr Lys Arg His Gln Asp Ala
65                  70                  75                  80

Val Glu Ala Phe Phe Lys Lys Ile Gly Met Asp Tyr Gly Lys Glu Val
                85                  90                  95

Glu Phe Pro Ala Phe Val Asp Gly Trp Lys Glu Leu Ala Asn His Asp
            100                 105                 110

Leu Lys Leu Trp Ser Gln Asn Lys Lys Ser Leu Ile Arg Asp Trp Gly

```
                115                 120                 125
Glu Ala Val Phe Asp Ile Phe Asp Lys Asp Gly Ser Gly Ser Ile Ser
        130                 135                 140
Leu Asp Glu Trp Lys Ala Tyr Gly Arg Ile Ser Gly Ile Cys Pro Ser
145                 150                 155                 160
Asp Glu Asp Ala Glu Lys Thr Phe Lys His Cys Asp Leu Asp Asn Ser
                165                 170                 175
Gly Lys Leu Asp Val Asp Glu Met Thr Arg Gln His Leu Gly Phe Trp
            180                 185                 190
Tyr Ala Leu Asp Pro Asn Ala Asp Gly Leu Tyr Gly Asn Phe Val Pro
        195                 200                 205

<210> SEQ ID NO 16
<211> LENGTH: 624
<212> TYPE: DNA
<213> ORGANISM: Clytia gregarium
<220> FEATURE:
<221> NAME/KEY: CDS
<222> LOCATION: (1)..(624)

<400> SEQUENCE: 16 gca act caa agc aaa ttt caa aac ttc aac atg gct gac act gca tca    48
Ala Thr Gln Ser Lys Phe Gln Asn Phe Asn Met Ala Asp Thr Ala Ser
1               5                   10                  15 aaa tac gcc gtc aaa ctc aga ccc aac ttc gac aac cca aaa tgg gtc    96
Lys Tyr Ala Val Lys Leu Arg Pro Asn Phe Asp Asn Pro Lys Trp Val
                20                  25                  30 aac aga cac aaa ttt atg ttc aac ttt ttg gac att aac ggc gac gga   144
Asn Arg His Lys Phe Met Phe Asn Phe Leu Asp Ile Asn Gly Asp Gly
            35                  40                  45 aaa atc act ttg gat gaa atc gtc tcc aaa gct tcc gat gac att tgc   192
Lys Ile Thr Leu Asp Glu Ile Val Ser Lys Ala Ser Asp Asp Ile Cys
        50                  55                  60 gcc aaa ctt gga gca aca cca gaa cag acc aaa cgt cac cag gat gct   240
Ala Lys Leu Gly Ala Thr Pro Glu Gln Thr Lys Arg His Gln Asp Ala
65                  70                  75                  80 gtc gaa gct ttc ttc aaa aag att ggt atg gat tat ggt aaa gaa gtc   288
Val Glu Ala Phe Phe Lys Lys Ile Gly Met Asp Tyr Gly Lys Glu Val
                85                  90                  95 gaa ttc cca gct ttt gtt gat gga tgg aaa gaa ctg gcc aat cat gac   336
Glu Phe Pro Ala Phe Val Asp Gly Trp Lys Glu Leu Ala Asn His Asp
                100                 105                 110 ttg aaa ctt tgg tct caa aac aag aaa tct ttg atc cgc gac tgg gga   384
Leu Lys Leu Trp Ser Gln Asn Lys Lys Ser Leu Ile Arg Asp Trp Gly
            115                 120                 125 gaa gct gtt ttc gac att ttt gac aaa gac gga agt ggc tca atc agt   432
Glu Ala Val Phe Asp Ile Phe Asp Lys Asp Gly Ser Gly Ser Ile Ser
        130                 135                 140 ttg gac gaa tgg aag gct tat gga cga atc tct gga atc tgc tca tca   480
Leu Asp Glu Trp Lys Ala Tyr Gly Arg Ile Ser Gly Ile Cys Ser Ser
145                 150                 155                 160 gac gaa gac gcc gaa aag acc ttc aaa cat tgc gat ttg gac aac agt   528
Asp Glu Asp Ala Glu Lys Thr Phe Lys His Cys Asp Leu Asp Asn Ser
                165                 170                 175 ggc aaa ctt gat gtt gat gag atg acc aga caa cat ttg gga ttc tgg   576
Gly Lys Leu Asp Val Asp Glu Met Thr Arg Gln His Leu Gly Phe Trp
            180                 185                 190 tac gcc ttg gac ccc aac gca gat ggt ctt tac ggc aat ttt gtt cct   624
Tyr Ala Leu Asp Pro Asn Ala Asp Gly Leu Tyr Gly Asn Phe Val Pro
        195                 200                 205
```

<210> SEQ ID NO 17
<211> LENGTH: 211
<212> TYPE: PRT
<213> ORGANISM: Clytia gregarium

<400> SEQUENCE: 17

```
Ser Thr Phe Ala Thr Gln Ser Lys Phe Gln Asn Phe Asn Met Ala Asp
1               5                   10                  15

Thr Ala Ser Lys Tyr Ala Val Lys Leu Arg Pro Asn Phe Asp Asn Pro
            20                  25                  30

Lys Trp Val Asn Arg His Lys Phe Met Phe Asn Phe Leu Asp Ile Asn
        35                  40                  45

Gly Asp Gly Lys Ile Thr Leu Asp Glu Ile Val Ser Lys Ala Ser Asp
    50                  55                  60

Asp Ile Cys Ala Lys Leu Gly Ala Thr Pro Glu Gln Thr Lys Arg His
65                  70                  75                  80

Gln Asp Ala Val Glu Ala Phe Phe Lys Lys Ile Gly Met Asp Tyr Gly
                85                  90                  95

Lys Glu Val Glu Phe Pro Ala Phe Val Asp Gly Trp Lys Glu Leu Ala
            100                 105                 110

Asn Tyr Asp Leu Lys Leu Trp Ser Gln Asn Lys Lys Ser Leu Ile Arg
        115                 120                 125

Asp Trp Gly Glu Ala Val Phe Asp Ile Phe Asp Lys Asp Gly Ser Gly
    130                 135                 140

Ser Ile Ser Leu Asp Glu Trp Lys Ala Tyr Gly Arg Ile Ser Gly Ile
145                 150                 155                 160

Cys Pro Ser Asp Glu Asp Ala Glu Lys Thr Phe Lys His Cys Asp Leu
                165                 170                 175

Asp Asn Ser Gly Lys Leu Asp Val Asp Glu Met Thr Arg Gln His Leu
            180                 185                 190

Gly Phe Trp Tyr Thr Leu Asp Pro Asn Ala Asp Gly Leu Tyr Gly Asn
        195                 200                 205

Phe Val Pro
    210
```

<210> SEQ ID NO 18
<211> LENGTH: 633
<212> TYPE: DNA
<213> ORGANISM: Clytia gregarium
<220> FEATURE:
<221> NAME/KEY: CDS
<222> LOCATION: (1)..(633)

<400> SEQUENCE: 18

```
tca act ttt gca act caa agc aaa ttt caa aac ttc aac atg gct gac     48
Ser Thr Phe Ala Thr Gln Ser Lys Phe Gln Asn Phe Asn Met Ala Asp
1               5                   10                  15 act gca tca aaa tac gcc gtc aaa ctc aga ccc aac ttc gac aac cca     96
Thr Ala Ser Lys Tyr Ala Val Lys Leu Arg Pro Asn Phe Asp Asn Pro
            20                  25                  30 aaa tgg gtc aac aga cac aaa ttt atg ttc aac ttt ttg gac att aac    144
Lys Trp Val Asn Arg His Lys Phe Met Phe Asn Phe Leu Asp Ile Asn
        35                  40                  45 ggc gac gga aaa atc act ttg gat gaa atc gtc tcc aaa gct tcg gat    192
Gly Asp Gly Lys Ile Thr Leu Asp Glu Ile Val Ser Lys Ala Ser Asp
    50                  55                  60 gac att tgc gcc aaa ctt gga gca aca cca gaa cag acc aaa cgt cac    240
Asp Ile Cys Ala Lys Leu Gly Ala Thr Pro Glu Gln Thr Lys Arg His
65                  70                  75                  80
```

```
cag gat gct gtc gaa gct ttc ttc aaa aag att ggt atg gat tat ggt      288
Gln Asp Ala Val Glu Ala Phe Phe Lys Lys Ile Gly Met Asp Tyr Gly
            85                  90                  95 aaa gaa gtc gaa ttc cca gct ttt gtt gat gga tgg aaa gaa ctg gcc      336
Lys Glu Val Glu Phe Pro Ala Phe Val Asp Gly Trp Lys Glu Leu Ala
   100                 105                 110 aat tat gac ttg aaa ctt tgg tct caa aac aag aaa tct ttg atc cgc      384
Asn Tyr Asp Leu Lys Leu Trp Ser Gln Asn Lys Lys Ser Leu Ile Arg
       115                 120                 125 gac tgg gga gaa gct gtt ttc gac att ttt gac aaa gac gga agt ggc      432
Asp Trp Gly Glu Ala Val Phe Asp Ile Phe Asp Lys Asp Gly Ser Gly
130                 135                 140 tca atc agt ttg gac gaa tgg aag gct tat gga cga atc tct gga atc      480
Ser Ile Ser Leu Asp Glu Trp Lys Ala Tyr Gly Arg Ile Ser Gly Ile
145                 150                 155                 160 tgc tca tca gac gaa gac gcc gaa aag acc ttc aaa cat tgc gat ttg      528
Cys Ser Ser Asp Glu Asp Ala Glu Lys Thr Phe Lys His Cys Asp Leu
                165                 170                 175 gac aac agt ggc aaa ctt gat gtt gat gag atg acc aga caa cat ttg      576
Asp Asn Ser Gly Lys Leu Asp Val Asp Glu Met Thr Arg Gln His Leu
            180                 185                 190 gga ttc tgg tac acc ttg gac ccc aac gct gat ggt ctt tac ggc aat      624
Gly Phe Trp Tyr Thr Leu Asp Pro Asn Ala Asp Gly Leu Tyr Gly Asn
        195                 200                 205 ttt gtt cct                                                          633
Phe Val Pro
    210

<210> SEQ ID NO 19
<211> LENGTH: 209
<212> TYPE: PRT
<213> ORGANISM: Clytia gregarium

<400> SEQUENCE: 19

Phe Ala Thr Gln Ser Lys Ser Gln Asn Phe Asn Met Ala Asp Thr Ala
1               5                   10                  15

Ser Lys Tyr Ala Val Lys Leu Arg Pro Asn Phe Asp Asn Pro Lys Trp
            20                  25                  30

Val Asn Arg His Lys Phe Met Phe Asn Phe Leu Asp Ile Asn Gly Asp
        35                  40                  45

Gly Lys Ile Thr Leu Asp Glu Ile Val Ser Ala Ser Asp Asp Ile
    50                  55                  60

Cys Ala Lys Leu Gly Ala Thr Pro Glu Gln Thr Lys Arg His Gln Asp
65                  70                  75                  80

Ala Val Glu Ala Phe Phe Lys Lys Ile Gly Met Asp Tyr Gly Lys Glu
                85                  90                  95

Val Glu Phe Pro Ala Phe Val Asp Gly Trp Lys Glu Leu Ala Asn Tyr
            100                 105                 110

Asp Leu Lys Leu Trp Ser Gln Asn Lys Lys Ser Leu Ile Arg Asp Trp
        115                 120                 125

Gly Glu Ala Val Phe Asp Ile Phe Asp Lys Asp Gly Ser Gly Ser Ile
    130                 135                 140

Ser Leu Asp Glu Trp Lys Ala Tyr Gly Arg Ile Ser Gly Ile Cys Pro
145                 150                 155                 160

Ser Asp Glu Asp Ala Glu Lys Thr Phe Lys His Cys Asp Leu Asp Asn
                165                 170                 175

Ser Gly Lys Leu Asp Val Asp Glu Met Thr Arg Gln His Leu Gly Phe
            180                 185                 190
```

```
Trp Tyr Thr Leu Asp Pro Asn Ala Asp Gly Leu Tyr Gly Asn Phe Val
        195                 200                 205
Pro

<210> SEQ ID NO 20
<211> LENGTH: 627
<212> TYPE: DNA
<213> ORGANISM: Clytia gregarium
<220> FEATURE:
<221> NAME/KEY: CDS
<222> LOCATION: (1)..(627)

<400> SEQUENCE: 20 ttt gca act caa agc aaa tct caa aac ttc aac atg gct gac act gca       48
Phe Ala Thr Gln Ser Lys Ser Gln Asn Phe Asn Met Ala Asp Thr Ala
1               5                   10                  15 tca aaa tac gcc gtc aaa ctc aga ccc aac ttc gac aac cca aaa tgg      96
Ser Lys Tyr Ala Val Lys Leu Arg Pro Asn Phe Asp Asn Pro Lys Trp
            20                  25                  30 gtc aac aga cac aaa ttt atg ttc aac ttt ttg gac att aac ggc gac     144
Val Asn Arg His Lys Phe Met Phe Asn Phe Leu Asp Ile Asn Gly Asp
        35                  40                  45 gga aaa atc act ttg gat gaa atc gtc tcc aaa gct tcg gat gac att     192
Gly Lys Ile Thr Leu Asp Glu Ile Val Ser Lys Ala Ser Asp Asp Ile
    50                  55                  60 tgc gcc aaa ctt gga gca aca cca gaa cag acc aaa cgt cac cag gat     240
Cys Ala Lys Leu Gly Ala Thr Pro Glu Gln Thr Lys Arg His Gln Asp
65                  70                  75                  80 gct gtc gaa gct ttc ttc aaa aaa att ggt atg gat tat ggt aaa gaa     288
Ala Val Glu Ala Phe Phe Lys Lys Ile Gly Met Asp Tyr Gly Lys Glu
                85                  90                  95 gtc gaa ttc cca gct ttt gtt gat gga tgg aaa gaa ctg gcc aat tat     336
Val Glu Phe Pro Ala Phe Val Asp Gly Trp Lys Glu Leu Ala Asn Tyr
            100                 105                 110 gac ttg aaa ctt tgg tct caa aac aag aaa tct ttg atc cgc gac tgg     384
Asp Leu Lys Leu Trp Ser Gln Asn Lys Lys Ser Leu Ile Arg Asp Trp
        115                 120                 125 gga gaa gct gtt ttc gac att ttt gac aaa gac gga agt ggc tca atc     432
Gly Glu Ala Val Phe Asp Ile Phe Asp Lys Asp Gly Ser Gly Ser Ile
    130                 135                 140 agt ttg gac gaa tgg aag gct tat gga cga atc tct gga atc tgc tca     480
Ser Leu Asp Glu Trp Lys Ala Tyr Gly Arg Ile Ser Gly Ile Cys Ser
145                 150                 155                 160 tca gac gaa gac gcc gaa aag acc ttc aaa cat tgc gat ttg gac aac     528
Ser Asp Glu Asp Ala Glu Lys Thr Phe Lys His Cys Asp Leu Asp Asn
                165                 170                 175 agt ggc aaa ctt gat gtc gat gag atg acc aga caa cat ttg gga ttc     576
Ser Gly Lys Leu Asp Val Asp Glu Met Thr Arg Gln His Leu Gly Phe
            180                 185                 190 tgg tac acc ttg gac ccg aac gct gat ggt ctt tac gga aac ttt gtc     624
Trp Tyr Thr Leu Asp Pro Asn Ala Asp Gly Leu Tyr Gly Asn Phe Val
        195                 200                 205 ccc                                                                   627
Pro

<210> SEQ ID NO 21
<211> LENGTH: 208
<212> TYPE: PRT
<213> ORGANISM: Clytia gregarium

<400> SEQUENCE: 21
```

```
Ala Thr Gln Ser Lys Ser Gln Asn Phe Asn Met Ala Asp Thr Ala Ser
1               5                   10                  15

Lys Tyr Ala Val Lys Leu Arg Pro Asn Phe Asp Asn Pro Lys Trp Val
            20                  25                  30

Asn Arg His Lys Phe Met Phe Asn Phe Leu Asp Ile Asn Gly Asp Gly
        35                  40                  45

Lys Ile Thr Leu Asp Glu Ile Val Ser Lys Ala Ser Asp Asp Ile Cys
    50                  55                  60

Ala Lys Leu Gly Ala Thr Pro Glu Gln Thr Lys Arg His Gln Asp Ala
65              70                  75                  80

Val Glu Ala Phe Phe Lys Lys Ile Gly Met Asp Tyr Gly Lys Glu Val
            85                  90                  95

Glu Phe Pro Ala Phe Val Asp Gly Trp Lys Glu Leu Ala Asn His Asp
            100                 105                 110

Leu Lys Leu Trp Ser Gln Asn Lys Lys Ser Leu Ile Arg Asp Trp Gly
        115                 120                 125

Glu Ala Val Phe Asp Ile Phe Asp Lys Asp Gly Ser Gly Ser Ile Ser
        130                 135                 140

Leu Asp Glu Trp Lys Ala Tyr Gly Arg Ile Ser Gly Ile Cys Pro Ser
145                 150                 155                 160

Asp Glu Asp Ala Glu Lys Thr Phe Lys His Cys Asp Leu Asp Asn Ser
            165                 170                 175

Gly Lys Leu Asp Val Asp Glu Met Thr Arg Gln His Leu Gly Phe Trp
            180                 185                 190

Tyr Thr Leu Asp Pro Asn Ala Asp Gly Leu Tyr Gly Asn Phe Val Pro
        195                 200                 205

<210> SEQ ID NO 22
<211> LENGTH: 624
<212> TYPE: DNA
<213> ORGANISM: Clytia gregarium
<220> FEATURE:
<221> NAME/KEY: CDS
<222> LOCATION: (1)..(624)

<400> SEQUENCE: 22 gca act caa agc aaa tct caa aac ttc aac atg gct gac act gca tca        48
Ala Thr Gln Ser Lys Ser Gln Asn Phe Asn Met Ala Asp Thr Ala Ser
1               5                   10                  15 aaa tac gcc gtc aaa ctc aga ccc aac ttc gac aac cca aaa tgg gtc        96
Lys Tyr Ala Val Lys Leu Arg Pro Asn Phe Asp Asn Pro Lys Trp Val
            20                  25                  30 aac aga cac aaa ttt atg ttc aac ttt ttg gac att aac ggc gac gga       144
Asn Arg His Lys Phe Met Phe Asn Phe Leu Asp Ile Asn Gly Asp Gly
        35                  40                  45 aaa atc act ttg gat gaa atc gtc tcc aaa gct tcg gat gac att tgc       192
Lys Ile Thr Leu Asp Glu Ile Val Ser Lys Ala Ser Asp Asp Ile Cys
    50                  55                  60 gcc aaa ctt gga gca aca cca gaa cag acc aaa cgt cac cag gat gct       240
Ala Lys Leu Gly Ala Thr Pro Glu Gln Thr Lys Arg His Gln Asp Ala
65              70                  75                  80 gtc gaa gct ttc ttc aaa aaa att ggt atg gat tat ggc aaa gaa gtc       288
Val Glu Ala Phe Phe Lys Lys Ile Gly Met Asp Tyr Gly Lys Glu Val
            85                  90                  95 gaa ttc cca gct ttt gtt gat gga tgg aaa gaa ctg gcc aat cat gac       336
Glu Phe Pro Ala Phe Val Asp Gly Trp Lys Glu Leu Ala Asn His Asp
            100                 105                 110 ttg aaa ctt tgg tct caa aac aag aaa tct ttg atc cgc gac tgg gga       384
Leu Lys Leu Trp Ser Gln Asn Lys Lys Ser Leu Ile Arg Asp Trp Gly
```

```
                 115                 120                 125
gaa gct gtt ttc gac att ttt gac aaa gac gga agt ggc tca atc agt      432
Glu Ala Val Phe Asp Ile Phe Asp Lys Asp Gly Ser Gly Ser Ile Ser
    130                 135                 140 ttg gac gaa tgg aag gct tat gga cga atc tct gga atc tgc tca tca      480
Leu Asp Glu Trp Lys Ala Tyr Gly Arg Ile Ser Gly Ile Cys Ser Ser
145                 150                 155                 160 gac gaa gac gcc gaa aag acc ttc aaa cat tgc gat ttg gac aac agt      528
Asp Glu Asp Ala Glu Lys Thr Phe Lys His Cys Asp Leu Asp Asn Ser
                165                 170                 175 ggc aaa ctt gat gtc gat gag atg acc aga caa cat ttg gga ttc tgg      576
Gly Lys Leu Asp Val Asp Glu Met Thr Arg Gln His Leu Gly Phe Trp
        180                 185                 190 tac acc ttg gac ccg aac gct gat ggt ctt tac gga aac ttt gtc ccc      624
Tyr Thr Leu Asp Pro Asn Ala Asp Gly Leu Tyr Gly Asn Phe Val Pro
            195                 200                 205

<210> SEQ ID NO 23
<211> LENGTH: 223
<212> TYPE: PRT
<213> ORGANISM: Artificial
<220> FEATURE:
<223> OTHER INFORMATION: Designed for recombinant protein production

<400> SEQUENCE: 23

Met Lys Lys Thr Ala Ile Ala Ile Ala Val Ala Leu Ala Gly Phe Ala
1               5                   10                  15

Thr Val Ala Gln Ala Ala Asn Ser His His His His His Gly Lys
            20                  25                  30

Leu His Met Glu Leu Asp Pro Asp Phe Ala Asn Pro Lys Trp Ile Asn
        35                  40                  45

Arg His Lys Phe Met Phe Asn Phe Leu Asp Ile Asn Gly Asn Gly Lys
    50                  55                  60

Ile Thr Leu Asp Glu Ile Val Ser Lys Ala Ser Asp Ile Cys Ala
65                  70                  75                  80

Lys Leu Asp Ala Thr Pro Glu Gln Thr Lys Arg His Gln Asp Ala Val
                85                  90                  95

Glu Ala Phe Phe Lys Lys Met Gly Met Asp Tyr Gly Lys Glu Val Ala
            100                 105                 110

Phe Pro Glu Phe Ile Lys Gly Trp Glu Glu Leu Ala Glu His Asp Leu
        115                 120                 125

Glu Leu Trp Ser Gln Asn Lys Ser Thr Leu Ile Arg Glu Trp Gly Asp
    130                 135                 140

Ala Val Phe Asp Ile Phe Asp Lys Asp Ala Ser Gly Ser Ile Ser Leu
145                 150                 155                 160

Asp Glu Trp Lys Ala Tyr Gly Arg Ile Ser Gly Ile Cys Pro Ser Asp
                165                 170                 175

Glu Asp Ala Glu Lys Thr Phe Lys His Cys Asp Leu Asp Asn Ser Gly
            180                 185                 190

Lys Leu Asp Val Asp Glu Met Thr Arg Gln His Leu Gly Phe Trp Tyr
        195                 200                 205

Thr Leu Asp Pro Thr Ser Asp Gly Leu Tyr Gly Asn Phe Val Pro
    210                 215                 220

<210> SEQ ID NO 24
<211> LENGTH: 672
<212> TYPE: DNA
<213> ORGANISM: Artificial
<220> FEATURE:
```

<223> OTHER INFORMATION: Designed for recombinant protein production
<220> FEATURE:
<221> NAME/KEY: CDS
<222> LOCATION: (1)..(672)

<400> SEQUENCE: 24

```
atg aaa aag aca gct atc gcg att gca gtg gca ctg gct ggt ttc gct         48
Met Lys Lys Thr Ala Ile Ala Ile Ala Val Ala Leu Ala Gly Phe Ala
1               5                   10                  15 acc gta gcg cag gcc gcg aat tcc cac cat cac cat cac cat ggt aag         96
Thr Val Ala Gln Ala Ala Asn Ser His His His His His His Gly Lys
            20                  25                  30 ctt cat atg gag ctc gat cct gat ttt gca aat cca aaa tgg atc aac        144
Leu His Met Glu Leu Asp Pro Asp Phe Ala Asn Pro Lys Trp Ile Asn
        35                  40                  45 aga cac aaa ttt atg ttc aac ttt ttg gac ata aac ggt aat ggg aaa        192
Arg His Lys Phe Met Phe Asn Phe Leu Asp Ile Asn Gly Asn Gly Lys
    50                  55                  60 atc aca tta gat gaa atc gtc tcc aaa gct tca gac gac att tgt gct        240
Ile Thr Leu Asp Glu Ile Val Ser Lys Ala Ser Asp Asp Ile Cys Ala
65                  70                  75                  80 aaa ctg gat gca aca cca gaa cag acc aaa cgt cac cag gat gct gtt        288
Lys Leu Asp Ala Thr Pro Glu Gln Thr Lys Arg His Gln Asp Ala Val
                85                  90                  95 gaa gcg ttt ttc aag aaa atg ggc atg gat tat ggt aaa gaa gtt gca        336
Glu Ala Phe Phe Lys Lys Met Gly Met Asp Tyr Gly Lys Glu Val Ala
            100                 105                 110 ttc cca gaa ttt att aag gga tgg gaa gag ttg gcc gaa cac gac ttg        384
Phe Pro Glu Phe Ile Lys Gly Trp Glu Glu Leu Ala Glu His Asp Leu
        115                 120                 125 gaa ctc tgg tct caa aac aaa agt aca ttg atc cgt gaa tgg gga gat        432
Glu Leu Trp Ser Gln Asn Lys Ser Thr Leu Ile Arg Glu Trp Gly Asp
    130                 135                 140 gct gtt ttc gac att ttc gac aaa gac gca agt ggc tca atc agt tta        480
Ala Val Phe Asp Ile Phe Asp Lys Asp Ala Ser Gly Ser Ile Ser Leu
145                 150                 155                 160 gac gaa tgg aag gct tac gga cga atc tct gga atc tgt cca tca gac        528
Asp Glu Trp Lys Ala Tyr Gly Arg Ile Ser Gly Ile Cys Pro Ser Asp
                165                 170                 175 gaa gac gct gag aag acg ttc aaa cat tgt gat ttg gac aac agt ggc        576
Glu Asp Ala Glu Lys Thr Phe Lys His Cys Asp Leu Asp Asn Ser Gly
            180                 185                 190 aaa ctt gat gtt gat gag atg acc agg caa cat tta ggc ttc tgg tac        624
Lys Leu Asp Val Asp Glu Met Thr Arg Gln His Leu Gly Phe Trp Tyr
        195                 200                 205 aca ttg gat cca act tct gat ggt ctt tat ggc aat ttt gtt ccc taa        672
Thr Leu Asp Pro Thr Ser Asp Gly Leu Tyr Gly Asn Phe Val Pro
    210                 215                 220
```

<210> SEQ ID NO 25
<211> LENGTH: 186
<212> TYPE: PRT
<213> ORGANISM: Clytia gregarium

<400> SEQUENCE: 25

```
Arg Pro Asn Phe Asp Asn Pro Lys Trp Val Asn Arg His Lys Phe Met
1               5                   10                  15

Phe Asn Phe Leu Asp Ile Asn Gly Asp Gly Lys Ile Thr Leu Asp Glu
            20                  25                  30

Ile Val Ser Lys Ala Ser Asp Asp Ile Cys Ala Lys Leu Gly Ala Thr
        35                  40                  45
```

```
Pro Glu Gln Thr Lys Arg His Gln Asp Ala Val Glu Ala Phe Phe Lys
    50                  55                  60
Lys Ile Gly Met Asp Tyr Gly Lys Glu Val Glu Phe Pro Ala Phe Val
65                  70                  75                  80
Asp Gly Trp Lys Glu Leu Ala Asn Tyr Asp Leu Lys Leu Trp Ser Gln
                85                  90                  95
Asn Lys Lys Ser Leu Ile Arg Asp Trp Gly Glu Ala Val Phe Asp Ile
                100                 105                 110
Phe Asp Lys Asp Gly Ser Gly Ser Ile Ser Leu Asp Glu Trp Lys Ala
                115                 120                 125
Tyr Gly Arg Ile Ser Gly Ile Cys Pro Ser Asp Glu Asp Ala Glu Lys
                130                 135                 140
Thr Phe Lys His Cys Asp Leu Asp Asn Ser Gly Lys Leu Asp Val Asp
145                 150                 155                 160
Glu Met Thr Arg Gln His Leu Gly Phe Trp Tyr Thr Leu Asp Pro Asn
                165                 170                 175
Ala Asp Gly Leu Tyr Gly Asn Phe Val Pro
                180                 185

<210> SEQ ID NO 26
<211> LENGTH: 558
<212> TYPE: DNA
<213> ORGANISM: Clytia gregarium
<220> FEATURE:
<221> NAME/KEY: CDS
<222> LOCATION: (1)..(558)

<400> SEQUENCE: 26 aga ccc aac ttc gac aac cca aaa tgg gtc aac aga cac aaa ttt atg      48
Arg Pro Asn Phe Asp Asn Pro Lys Trp Val Asn Arg His Lys Phe Met
1               5                   10                  15 ttc aac ttt ttg gac att aac ggc gac gga aaa atc act ttg gat gaa     96
Phe Asn Phe Leu Asp Ile Asn Gly Asp Gly Lys Ile Thr Leu Asp Glu
            20                  25                  30 atc gtc tcc aaa gct tcg gat gac att tgc gcc aaa ctt gga gca aca    144
Ile Val Ser Lys Ala Ser Asp Asp Ile Cys Ala Lys Leu Gly Ala Thr
        35                  40                  45 cca gaa cag acc aaa cgt cac cag gat gct gtc gaa gct ttc ttc aaa    192
Pro Glu Gln Thr Lys Arg His Gln Asp Ala Val Glu Ala Phe Phe Lys
    50                  55                  60 aag att ggt atg gat tat ggt aaa gaa gtc gaa ttc cca gct ttt gtt    240
Lys Ile Gly Met Asp Tyr Gly Lys Glu Val Glu Phe Pro Ala Phe Val
65                  70                  75                  80 gat gga tgg aaa gaa ctg gcc aat tat gac ttg aaa ctt tgg tct caa    288
Asp Gly Trp Lys Glu Leu Ala Asn Tyr Asp Leu Lys Leu Trp Ser Gln
                85                  90                  95 aac aag aaa tct ttg atc cgc gac tgg gga gaa gct gtt ttc gac att    336
Asn Lys Lys Ser Leu Ile Arg Asp Trp Gly Glu Ala Val Phe Asp Ile
                100                 105                 110 ttt gac aaa gac gga agt ggc tca atc agt ttg gac gaa tgg aag gct    384
Phe Asp Lys Asp Gly Ser Gly Ser Ile Ser Leu Asp Glu Trp Lys Ala
                115                 120                 125 tat gga cga atc tct gga atc tgc tca tca gac gaa gac gcc gaa aag    432
Tyr Gly Arg Ile Ser Gly Ile Cys Ser Ser Asp Glu Asp Ala Glu Lys
                130                 135                 140 acc ttc aaa cat tgc gat ttg gac aac agt ggc aaa ctt gat gtt gat    480
Thr Phe Lys His Cys Asp Leu Asp Asn Ser Gly Lys Leu Asp Val Asp
145                 150                 155                 160 gag atg acc aga caa cat ttg gga ttc tgg tac acc ttg gac ccc aac    528
Glu Met Thr Arg Gln His Leu Gly Phe Trp Tyr Thr Leu Asp Pro Asn
```

```
                    165                 170                 175
gct gat ggt ctt tac ggc aat ttt gtt cct                               558
Ala Asp Gly Leu Tyr Gly Asn Phe Val Pro
                180                 185

<210> SEQ ID NO 27
<211> LENGTH: 223
<212> TYPE: PRT
<213> ORGANISM: Artificial
<220> FEATURE:
<223> OTHER INFORMATION: Designed for recombinant protein production

<400> SEQUENCE: 27

Met Lys Lys Thr Ala Ile Ala Ile Ala Val Ala Leu Ala Gly Phe Ala
1               5                   10                  15

Thr Val Ala Gln Ala Ala Asn Ser His His His His His Gly Lys
            20                  25                  30

Leu His Met Glu Leu Arg Pro Asn Phe Asp Asn Pro Lys Trp Val Asn
        35                  40                  45

Arg His Lys Phe Met Phe Asn Phe Leu Asp Ile Asn Gly Asp Gly Lys
    50                  55                  60

Ile Thr Leu Asp Glu Ile Val Ser Lys Ala Ser Asp Asp Ile Cys Ala
65                  70                  75                  80

Lys Leu Gly Ala Thr Pro Glu Gln Thr Lys Arg His Gln Asp Ala Val
                85                  90                  95

Glu Ala Phe Phe Lys Lys Ile Gly Met Asp Tyr Gly Lys Glu Val Glu
            100                 105                 110

Phe Pro Ala Phe Val Asp Gly Trp Lys Glu Leu Ala Asn Tyr Asp Leu
        115                 120                 125

Lys Leu Trp Ser Gln Asn Lys Lys Ser Leu Ile Arg Asp Trp Gly Glu
    130                 135                 140

Ala Val Phe Asp Ile Phe Asp Lys Asp Gly Ser Gly Ser Ile Ser Leu
145                 150                 155                 160

Asp Glu Trp Lys Ala Tyr Gly Arg Ile Ser Gly Ile Cys Pro Ser Asp
                165                 170                 175

Glu Asp Ala Glu Lys Thr Phe Lys His Cys Asp Leu Asp Asn Ser Gly
            180                 185                 190

Lys Leu Asp Val Asp Glu Met Thr Arg Gln His Leu Gly Phe Trp Tyr
        195                 200                 205

Thr Leu Asp Pro Asn Ala Asp Gly Leu Tyr Gly Asn Phe Val Pro
    210                 215                 220

<210> SEQ ID NO 28
<211> LENGTH: 672
<212> TYPE: DNA
<213> ORGANISM: Artificial
<220> FEATURE:
<223> OTHER INFORMATION: Designed for recombinant protein production
<220> FEATURE:
<221> NAME/KEY: CDS
<222> LOCATION: (1)..(672)

<400> SEQUENCE: 28 atg aaa aag aca gct atc gcg att gca gtg gca ctg gct ggt ttc gct     48
Met Lys Lys Thr Ala Ile Ala Ile Ala Val Ala Leu Ala Gly Phe Ala
1               5                   10                  15 acc gta gcg cag gcc gcg aat tcc cac cat cac cat cac cat ggt aag     96
Thr Val Ala Gln Ala Ala Asn Ser His His His His His His Gly Lys
            20                  25                  30 ctt cat atg gag ctc aga ccc aac ttc gac aac cca aaa tgg gtc aac    144
```

-continued

| | | | | | | | | | | | | | | | |
|---|---|---|---|---|---|---|---|---|---|---|---|---|---|---|---|
| | Leu | His | Met | Glu | Leu | Arg | Pro | Asn | Phe | Asp | Asn | Pro | Lys | Trp | Val Asn |
| | | 35 | | | | 40 | | | | | 45 | | | | |

```
aga cac aaa ttt atg ttc aac ttt ttg gac att aac ggc gac gga aaa      192
Arg His Lys Phe Met Phe Asn Phe Leu Asp Ile Asn Gly Asp Gly Lys
 50                  55                  60 atc act ttg gat gaa atc gtc tcc aaa gct tcg gat gac att tgc gcc      240
Ile Thr Leu Asp Glu Ile Val Ser Lys Ala Ser Asp Asp Ile Cys Ala
 65                  70                  75                  80 aaa ctt gga gca aca cca gaa cag acc aaa cgt cac cag gat gct gtc      288
Lys Leu Gly Ala Thr Pro Glu Gln Thr Lys Arg His Gln Asp Ala Val
                 85                  90                  95 gaa gct ttc ttc aaa aag att ggt atg gat tat ggt aaa gaa gtc gaa      336
Glu Ala Phe Phe Lys Lys Ile Gly Met Asp Tyr Gly Lys Glu Val Glu
            100                 105                 110 ttc cca gct ttt gtt gat gga tgg aaa gaa ctg gcc aat tat gac ttg      384
Phe Pro Ala Phe Val Asp Gly Trp Lys Glu Leu Ala Asn Tyr Asp Leu
        115                 120                 125 aaa ctt tgg tct caa aac aag aaa tct ttg atc cgc gac tgg gga gaa      432
Lys Leu Trp Ser Gln Asn Lys Lys Ser Leu Ile Arg Asp Trp Gly Glu
130                 135                 140 gct gtt ttc gac att ttt gac aaa gac gga agt ggc tca atc agt ttg      480
Ala Val Phe Asp Ile Phe Asp Lys Asp Gly Ser Gly Ser Ile Ser Leu
145                 150                 155                 160 gac gaa tgg aag gct tat gga cga atc tct gga atc tgc tca tca gac      528
Asp Glu Trp Lys Ala Tyr Gly Arg Ile Ser Gly Ile Cys Ser Ser Asp
                165                 170                 175 gaa gac gcc gaa aag acc ttc aaa cat tgc gat ttg gac aac agt ggc      576
Glu Asp Ala Glu Lys Thr Phe Lys His Cys Asp Leu Asp Asn Ser Gly
            180                 185                 190 aaa ctt gat gtt gat gag atg acc aga caa cat ttg gga ttc tgg tac      624
Lys Leu Asp Val Asp Glu Met Thr Arg Gln His Leu Gly Phe Trp Tyr
        195                 200                 205 acc ttg gac ccc aac gct gat ggt ctt tac ggc aat ttt gtt cct taa      672
Thr Leu Asp Pro Asn Ala Asp Gly Leu Tyr Gly Asn Phe Val Pro
    210                 215                 220

<210> SEQ ID NO 29
<211> LENGTH: 34
<212> TYPE: PRT
<213> ORGANISM: Clytia gregarium

<400> SEQUENCE: 29

Asn Arg Leu Leu Ser Met Ser Ala Leu Ala Ala Arg Ser Arg Leu Gln
 1               5                  10                  15

Arg Thr Ala Asn Phe His Thr Ser Ile Leu Leu Ala Thr Asp Ser Lys
            20                  25                  30

Tyr Ala

<210> SEQ ID NO 30
<211> LENGTH: 102
<212> TYPE: DNA
<213> ORGANISM: Clytia gregarium
<220> FEATURE:
<221> NAME/KEY: CDS
<222> LOCATION: (1)..(102)

<400> SEQUENCE: 30 aat cgt ctt ctt tcc atg tcg gct tta gct gca aga tca aga ttg caa       48
Asn Arg Leu Leu Ser Met Ser Ala Leu Ala Ala Arg Ser Arg Leu Gln
 1               5                  10                  15 cgc aca gca aat ttt cac acc agc ata ctg ttg gct aca gat tca aaa       96
Arg Thr Ala Asn Phe His Thr Ser Ile Leu Leu Ala Thr Asp Ser Lys
```

```
                          20                  25                  30
tac gcg                                                                   102
Tyr Ala <210> SEQ ID NO 31
<211> LENGTH: 46
<212> TYPE: PRT
<213> ORGANISM: Clytia gregarium

<400> SEQUENCE: 31

Lys Lys Gly Gln Glu Ile Lys Met Leu Trp Phe Thr Asn Arg Leu Leu
1               5                   10                  15

Ser Met Ser Ala Leu Ala Ala Arg Ser Arg Leu Gln Arg Thr Ala Asn
            20                  25                  30

Phe His Thr Ser Ile Leu Leu Ala Thr Asp Ser Lys Tyr Ala
        35                  40                  45

<210> SEQ ID NO 32
<211> LENGTH: 138
<212> TYPE: DNA
<213> ORGANISM: Clytia gregarium
<220> FEATURE:
<221> NAME/KEY: CDS
<222> LOCATION: (1)..(138)

<400> SEQUENCE: 32 aaa aaa gga caa gaa atc aag atg ctt tgg ttt aca aat cgt ctt ctt          48
Lys Lys Gly Gln Glu Ile Lys Met Leu Trp Phe Thr Asn Arg Leu Leu
1               5                   10                  15 tcc atg tca gct tta gct gca aga tca aga tta caa cgc aca gca aat          96
Ser Met Ser Ala Leu Ala Ala Arg Ser Arg Leu Gln Arg Thr Ala Asn
            20                  25                  30 ttt cac acc agc ata ctg ttg gct aca gat tca aaa tac gca                 138
Phe His Thr Ser Ile Leu Leu Ala Thr Asp Ser Lys Tyr Ala
        35                  40                  45

<210> SEQ ID NO 33
<211> LENGTH: 27
<212> TYPE: DNA
<213> ORGANISM: Artificial
<220> FEATURE:
<223> OTHER INFORMATION: Primer

<400> SEQUENCE: 33
aattcccacc atcaccatca ccatggt                                            27

<210> SEQ ID NO 34
<211> LENGTH: 22
<212> TYPE: DNA
<213> ORGANISM: Artificial
<220> FEATURE:
<223> OTHER INFORMATION: Primer

<400> SEQUENCE: 34
agcttaccat ggtgatggtg gg                                                 22

<210> SEQ ID NO 35
<211> LENGTH: 27
<212> TYPE: DNA
<213> ORGANISM: Artificial
<220> FEATURE:
<223> OTHER INFORMATION: Primer

<400> SEQUENCE: 35
ggcgagctcg atcctgattt tgcaaat                                            27
```

```
<210> SEQ ID NO 36
<211> LENGTH: 30
<212> TYPE: DNA
<213> ORGANISM: Artificial
<220> FEATURE:
<223> OTHER INFORMATION: Primer

<400> SEQUENCE: 36
cggctcgagt taaccaacaa aattgccgta                                    30

<210> SEQ ID NO 37
<211> LENGTH: 27
<212> TYPE: DNA
<213> ORGANISM: Artificial
<220> FEATURE:
<223> OTHER INFORMATION: Primer

<400> SEQUENCE: 37
ggcgagctca gacccaactt cgacaac                                       27

<210> SEQ ID NO 38
<211> LENGTH: 27
<212> TYPE: DNA
<213> ORGANISM: Artificial
<220> FEATURE:
<223> OTHER INFORMATION: Primer

<400> SEQUENCE: 38
ggcgagctca gacccaactt cgacaac                                       27
```

CALCIUM-BINDING PHOTOPROTEIN, GENE ENCODING THE SAME, AND USE THEREOF

CROSS REFERENCE TO RELATED APPLICATIONS

This is a Divisional application, which claims priority to U.S. Non-Provisional application Ser. No. 12/645,226 filed on Dec. 22, 2009, which is a Divisional application, which claims priority to U.S. Non-Provisional application Ser. No. 11/826,915, filed on Jul. 19, 2007; which is a U.S. Non-Provisional Application, which claims priority to U.S. Provisional Patent Application No. 60/831,939, filed Jul. 20, 2006, the contents of which are all herein expressly incorporated herein by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

1. Field of the Invention

The invention relates to calcium-binding photoproteins, genes encoding the same, and use thereof.

2. Related Art

Calcium-binding photoproteins are photoproteins in which an apoprotein and a peroxide of a light-emitting substrate exist in the state of a complex formed therefrom. Calcium-binding photoproteins have the quality of momentarily emitting light on bonding with a calcium ion.

Known calcium-binding photoproteins include aequorin, obelin, clytin, mitrocomin, mineopsin and bervoin. Of these, aequorin is a typical calcium-binding photoprotein, the higher-order structure and light-emitting mechanism of which have been reported in detail (see, for example, Inouye et al., Proc. Natl. Acad. Sci. USA, 82, 3154-3158 (1985); Head et al., Nature, 405, 372-376 (2000)). Due to aequorin having a very high sensitivity to calcium ions, it is used to detect and assay trace amounts of calcium ions, and to measure changes in the intracellular concentration of calcium ions.

Clytin is a calcium-binding photoprotein obtained from the luminescent jellyfish *Clytia gregarium* (see Inouye, S, and Tsuji, F. I., FEBS Lett., 315, 343-346 (1993). Clytin exists in the state of a complex formed from apoclytin and a peroxide of the light-emitting substrate coelenterazine. When clytin bonds with a calcium ion, it momentarily emits light and forms coelenteramide—an oxide of coelenterazine, and carbon dioxide.

SUMMARY OF THE INVENTION

There currently exists a desire for calcium-binding photoproteins which have a high maximum luminescence intensity (Imax) per unit weight of protein and a high S/N ratio, and which thus enable the more sensitive detection of luminescence.

It has been observed that proteins having the amino acid sequence of SEQ ID NO: 1 or an amino acid sequence with, in the amino acid sequence of SEQ ID NO: 1, one or more deleted, substituted, inserted and/or added amino acid, are able to bond with a peroxide of coelenterazine or a peroxide of a coelenterazine derivative to form a holoprotein which emits light under the action of a calcium ion. It has also been observed that the light emitted when the holoprotein thus obtained bonds with a calcium ion has a higher maximum luminescence intensity (Imax) per unit weight of protein and a higher S/N ratio than known photoproteins.

The invention includes:

(1) A protein selected from the following items (a) to (h):

(a) a protein which includes the amino acid sequence set forth in SEQ ID NO: 1;

(b) a protein which includes an amino acid sequence with, in the amino acid sequence of SEQ ID NO: 1, one or more deleted, substituted, inserted and/or added amino acid, and which has the ability to bond with a peroxide of coelenterazine or a peroxide of a coelenterazine derivative so as to form a holoprotein that emits light under the action of a calcium ion;

(c) a protein which includes an amino acid sequence that is at least approximately 90% identical to the amino acid sequence of SEQ ID NO: 1, and which has the ability to bond with a peroxide of coelenterazine or a peroxide of a coelenterazine derivative so as to form a holoprotein that emits light under the action of a calcium ion;

(d) a protein which includes an amino acid sequence encoded by a polynucleotide that hybridizes under stringent conditions to a polynucleotide having a nucleotide sequence complementary to the nucleotide sequence of SEQ ID NO: 2, and which has the ability to bond with a peroxide of coelenterazine or a peroxide of a coelenterazine derivative so as to form a holoprotein that emits light under the action of a calcium ion;

(e) a protein which includes the amino acid sequence of SEQ ID NO: 1, and which has the ability to bond with a peroxide of coelenterazine or a peroxide of a coelenterazine derivative so as to form a holoprotein that emits light under the action of a calcium ion;

(f) a protein which includes an amino acid sequence with, in the amino acid sequence of SEQ ID NO: 1, one or more deleted, substituted, inserted and/or added amino acid, and which has the ability to bond with a peroxide of coelenterazine or a peroxide of a coelenterazine derivative so as to form a holoprotein that emits light under the action of a calcium ion;

(g) a protein which includes an amino acid sequence that is at least approximately 90% identical to the amino acid sequence of SEQ ID NO: 1, and which has the ability to bond with a peroxide of coelenterazine or a peroxide of a coelenterazine derivative so as to form a holoprotein that emits light under the action of a calcium ion; and (h) a protein which includes an amino acid sequence encoded by a polynucleotide that hybridizes under stringent conditions to a polynucleotide having a nucleotide sequence complementary to the nucleotide sequence of SEQ ID NO: 2, and which has the ability to bond with a peroxide of coelenterazine or a peroxide of a coelenterazine derivative so as to form a holoprotein that emits light under the action of a calcium ion.

(2) The protein of item (1) above which is selected from the following items (a) to (h):

(a) a protein which includes the amino acid sequence set forth in SEQ ID NOS: 1, 3, 5, 7, 9 or 11;

(b) a protein which includes an amino acid sequence with, in the amino acid sequence of SEQ ID NOS: 1, 3, 5, 7, 9 or 11, from one to sixteen deleted, substituted, inserted and/or added amino acids, and which has the ability to bond with a peroxide of coelenterazine or a peroxide of a coelenterazine derivative so as to form a holoprotein that emits light under the action of a calcium ion;

(c) a protein which includes an amino acid sequence that is at least approximately 90% identical to the amino acid sequence of SEQ ID NO: 1, 3, 5, 7, 9 or 11, and which has the ability to bond with a peroxide of coelenterazine or a peroxide of a coelenterazine derivative so as to form a holoprotein that emits light under the action of a calcium ion;

(d) a protein which includes an amino acid sequence encoded by a polynucleotide that hybridizes under highly stringent conditions to a polynucleotide having a nucleotide sequence complementary to the nucleotide sequence of SEQ ID NOS: 2, 4, 6, 8, 10 or 12, and which has the ability to bond with a peroxide of coelenterazine or a peroxide of a coelenterazine derivative so as to form a holoprotein that emits light under the action of a calcium ion;

(e) a protein which includes the amino acid sequence of SEQ ID NOS: 1, 3, 5, 7, 9 or 11, and which has the ability to bond with a peroxide of coelenterazine or a peroxide of a coelenterazine derivative so as to form a holoprotein that emits light under the action of a calcium ion;

(f) a protein which includes an amino acid sequence with, in the amino acid sequence of SEQ ID NOS: 1, 3, 5, 7, 9 or 11, from one to sixteen deleted, substituted, inserted and/or added amino acids, and which has the ability to bond with a peroxide of coelenterazine or a peroxide of a coelenterazine derivative so as to form a holoprotein that emits light under the action of a calcium ion;

(g) a protein which includes an amino acid sequence that is at least approximately 90% identical to the amino acid sequence of SEQ ID NOS: 1, 3, 5, 7, 9 or 11, and which has the ability to bond with a peroxide of coelenterazine or a peroxide of a coelenterazine derivative so as to form a holoprotein that emits light under the action of a calcium ion; and (h) a protein which includes an amino acid sequence encoded by a polynucleotide that hybridizes under highly stringent conditions with a polynucleotide having a nucleotide sequence complementary to the nucleotide sequence of SEQ ID NOS: 2, 4, 6, 8, 10 or 12, and which has the ability to bond with a peroxide of coelenterazine or a peroxide of a coelenterazine derivative so as to form a holoprotein that emits light under the action of a calcium ion.

(3) The protein of item (1) above which is selected from the following items (a) to (h):

(a) a protein which includes the amino acid sequence set forth in SEQ ID NO: 1, 3, 5, 7, 9 or 11;

(b) a protein which includes an amino acid sequence with, in the amino acid sequence of SEQ ID NOS: 1, 3, 5, 7, 9 or 11, from one to six deleted, substituted, inserted and/or added amino acids, and which has the ability to bond with a peroxide of coelenterazine or a peroxide of a coelenterazine derivative so as to form a holoprotein that emits light under the action of a calcium ion;

(c) a protein which includes an amino acid sequence that is at least approximately 95% identical to the amino acid sequence of SEQ ID NOS: 1, 3, 5, 7, 9 or 11, and which has the ability to bond with a peroxide of coelenterazine or a peroxide of a coelenterazine derivative so as to form a holoprotein that emits light under the action of a calcium ion;

(d) a protein which includes an amino acid sequence encoded by a polynucleotide that hybridizes under highly stringent conditions to a polynucleotide having a nucleotide sequence complementary to the nucleotide sequence of SEQ ID NOS: 2, 4, 6, 8, 10 or 12, and which has the ability to bond with a peroxide of coelenterazine or a peroxide of a coelenterazine derivative so as to form a holoprotein that emits light under the action of a calcium ion;

(e) a protein which includes the amino acid sequence of SEQ ID NOS: 1, 3, 5, 7, 9 or 11, and which has the ability to bond with a peroxide of coelenterazine or a peroxide of a coelenterazine derivative so as to form a holoprotein that emits light under the action of a calcium ion;

(f) a protein which includes an amino acid sequence with, in the amino acid sequence of SEQ ID NOS: 1, 3, 5, 7, 9 or 11, from one to six deleted, substituted, inserted and/or added amino acids, and which has the ability to bond with a peroxide of coelenterazine or a peroxide of a coelenterazine derivative so as to form a holoprotein that emits light under the action of a calcium ion;

(g) a protein which includes an amino acid sequence that is at least approximately 95% identical to the amino acid sequence of SEQ ID NOS: 1, 3, 5, 7, 9 or 11, and which has the ability to bond with a peroxide of coelenterazine or a peroxide of a coelenterazine derivative so as to form a holoprotein that emits light under the action of a calcium ion; and (h) a protein which includes an amino acid sequence encoded by a polynucleotide that hybridizes under highly stringent conditions to a polynucleotide having a nucleotide sequence complementary to the nucleotide sequence of SEQ ID NOS: 2, 4, 6, 8, 10 or 12, and which has the ability to bond with a peroxide of a coelenterazine or a peroxide of a coelenterazine derivative so as to form a holoprotein that emits light under the action of a calcium ion.

(4) The protein of item (1) above which is:

(a) a protein including the amino acid sequence set forth in SEQ ID NOS: 1, 3, 5, 7, 9 or 11; or (b) a protein which includes the amino acid sequence of SEQ ID NOS: 1, 3, 5, 7, 9 or 11, and which has the ability to bond with a peroxide of coelenterazine or a peroxide of a coelenterazine derivative so as to form a holoprotein that emits light under the action of a calcium ion.

(5) The protein of any of items (1) to (4) above, further including, for purification, a peptide sequence and/or a secretory signal peptide sequence.

(6) A holoprotein composed of the protein of any of items (1) to (5) above and a peroxide of coelenterazine or a peroxide of a coelenterazine derivative.

(7) A polynucleotide encoding the protein of any of items (1) to (5) above.

(8) The polynucleotide of item (7) above which is selected from the following items (a) to (f):

(a) a polynucleotide which includes the nucleotide sequence set forth in SEQ ID NOS: 2, 4, 6, 8, 10 or 12;

(b) a polynucleotide which hybridizes under stringent conditions to a polynucleotide having a nucleotide sequence complementary to the nucleotide sequence of SEQ ID NOS: 2, 4, 6, 8, 10 or 12, and which encodes a protein having the ability to bond with a peroxide of coelenterazine or a peroxide of a coelenterazine derivative so as to form a holoprotein that emits light under the action of a calcium ion;

(c) a polynucleotide encoding a protein including the amino acid sequence of SEQ ID NOS: 1, 3, 5, 7, 9 or 11;

(d) a polynucleotide encoding a protein which includes an amino acid sequence with, in the amino acid sequence of SEQ ID NOS: 1, 3, 5, 7, 9 or 11, one or more deleted, substituted, inserted and/or added amino acid, and which has the ability to bond with a peroxide of coelenterazine or a peroxide of a coelenterazine derivative so as to form a holoprotein that emits light under the action of a calcium ion;

(e) a polynucleotide encoding a protein which includes the amino acid sequence of SEQ ID NOS: 1, 3, 5, 7, 9 or 11; and (f) a polynucleotide encoding a protein which includes an amino acid sequence with, in the amino acid sequence of SEQ ID NOS: 1, 3, 5, 7, 9 or 11, one or more deleted, substituted, inserted and/or added amino acid, and which has the ability to bond with a peroxide of coelenterazine or a peroxide of a coelenterazine derivative so as to form a holoprotein that emits light under the action of a calcium ion.

(9) The polynucleotide of item (7) above which is selected from the following items (a) to (f):

(a) a polynucleotide which includes the nucleotide sequence set forth in SEQ ID NOS: 2, 4, 6, 8, 10 or 12;

(b) a polynucleotide which hybridizes under highly stringent conditions to a polynucleotide having a nucleotide sequence complementary to the nucleotide sequence of SEQ ID NOS: 2, 4, 6, 8, 10 or 12, and which encodes a protein having the ability to bond with a peroxide of coelenterazine or a peroxide of a coelenterazine derivative so as to form a holoprotein that emits light under the action of a calcium ion;

(c) a polynucleotide encoding a protein which includes the amino acid sequence of SEQ ID NOS: 1, 3, 5, 7, 9 or 11;

(d) a polynucleotide encoding a protein which includes an amino acid sequence with, in the amino acid sequence of SEQ ID NOS: 1, 3, 5, 7, 9 or 11, from one to sixteen deleted, substituted, inserted and/or added amino acids, and which has the ability to bond with a peroxide of coelenterazine or a peroxide of a coelenterazine derivative so as to form a holoprotein that emits light under the action of a calcium ion;

(e) a polynucleotide encoding a protein which includes the amino acid sequence of SEQ ID NOS: 1, 3, 5, 7, 9 or 11; and (f) a polynucleotide encoding a protein which includes an amino acid sequence with, in the amino acid sequence of SEQ ID NOS: 1, 3, 5, 7, 9 or 11, from one to sixteen deleted, substituted, inserted and/or added amino acids, and which has the ability to bond with a peroxide of coelenterazine or a peroxide of a coelenterazine derivative so as to form a holoprotein that emits light under the action of a calcium ion.

(10) The polynucleotide of item (7) above which is selected from the following items (a) to (c):

(a) a polynucleotide which includes the nucleotide sequence set forth in SEQ ID NOS: 2, 4, 6, 8, 10 or 12;

(b) a polynucleotide encoding a protein which includes the amino acid sequence of SEQ ID NO: 1, 3, 5, 7, 9 or 11; and (c) a polynucleotide encoding a protein which includes the amino acid sequence of SEQ ID NOS: 1, 3, 5, 7, 9 or 11.

(11) A recombinant vector which includes the polynucleotide of any of items (7) to (10) above.

(12) A transformant having inserted therein the recombinant vector of item (11) above.

(13) A method for producing the protein of any of items (1) to (5) above, which method includes a step of culturing the transformant of item (12) above so as to induce the transformant to produce the protein of any of items (1) to (5) above.

(14) A kit which includes the protein of any of items (1) to (5) above or the holoprotein of item (6) above.

(15) A kit which includes the polynucleotide of any of items (7) to (10) above, the recombinant vector of item (11) above, or the transformant of item (12) above.

(16) A method for detecting or assaying calcium ions, which method includes use of the protein of any one of items (1) to (5) above or the holoprotein of item (6) above.

(17) A method for measuring activity of a sequence which participates in promoter control, which method includes use of the polynucleotide of any one of items (7) to (10) above as a reporter gene.

(18) A method for measuring changes in intracellular calcium concentration, which method includes a step of inducing expression of the polynucleotide of any of items (7) to (10) above within a cell so as to form a photoprotein.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings:

FIG. 2 is a diagram comparing the amino acid sequences inferred from the nucleotide sequences of the cDNA clones pCL11, pCL41, pCL51R and pCL81 of the CL-I group and the cDNA clones pCL21, pCL31 and pCL61R of the CL-II group;

FIG. 3 are schematic diagrams showing recombinant vectors according to the invention. FIG. 3A shows the basic vector piP-H6-M(11). FIG. 3B shows the apoCL-II expression vector piP-H-CLII and the apoCL-I expression vector piP-H-CLI;

DESCRIPTION OF THE PREFERRED EMBODIMENTS

Figure 1:
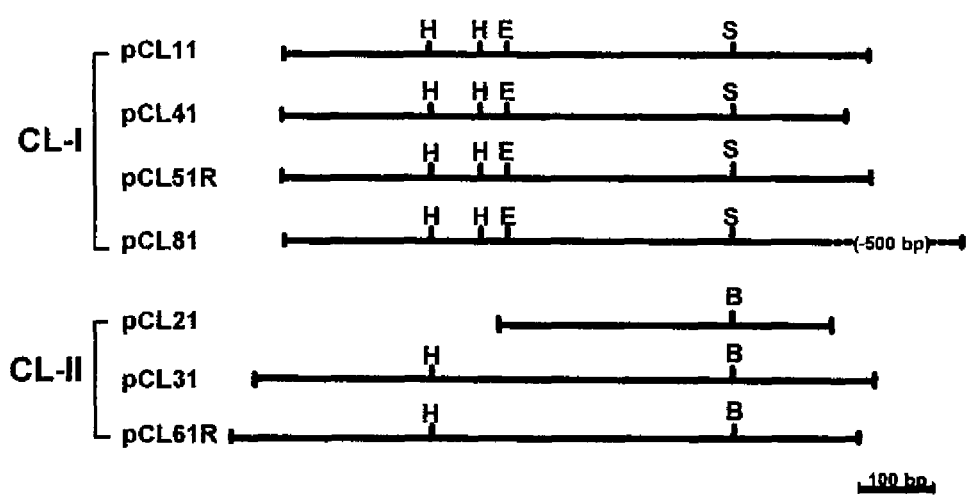
FIG. 1 is a diagram showing the restriction enzyme map-based classification of CL-I and CL-II derived from the luminescent jelly fish *Clytia gregarium*.

Embodiments of the invention are described in detail below.

Protein of the Invention

"Protein of the invention" refers herein to a protein having the amino acid sequence set forth in SEQ ID NO: 1 and to proteins which possess a substantially similar activity or ability as the protein having the amino acid sequence of SEQ ID NO: 1. In the present specification, the protein having the amino acid sequence of SEQ ID NO: 1 and proteins which possess a substantially similar activity or ability as the protein having the amino acid sequence of SEQ ID NO: 1 are referred to as "apoCL-II."

"Substantially similar activity or ability" refers to any of the following, for example: (i) the ability for the foregoing protein to bond with a peroxide of coelenterazine or a peroxide of a coelenterazine derivative so as to form a holoprotein; (ii) the ability for the foregoing protein to bond with a peroxide of coelenterazine or a peroxide of a coelenterazine derivative so as to form a holoprotein that emits light under the action of a calcium ion; (iii) a maximum intensity (Imax) by the luminescence that arises from the bonding of the foregoing holoprotein with calcium ions which is at least approximately ¼, preferably at least approximately ⅓, more preferably at least approximately ½, and even more preferably at least approximately 1/1.5, the maximum luminescence intensity (Imax) of the protein having the amino acid sequence of SEQ ID NO: 1; and (iv) a half-life ($T_{1/2}$, in seconds) for the luminescence that arises from the bonding of the foregoing holoprotein with calcium ions which is not more than 4 times, preferably not more than approximately 3 times, more preferably not more than approximately 2 times, and even more preferably not more than approximately 1.5 times, the half-life ($T_{1/2}$, in seconds) of the protein having the amino acid sequence of SEQ ID NO: 1. Measurement of the above luminescence activity and luminescence pattern may be carried out by the methods described in, for example, Shimomura, O. et al., Biochem. J., 251, 405-410 (1988) and Shimomura, O. et al., Biochem. J., 261, 913-920 (1989). Specifically, a luminescent reaction is initiated by adding a calcium solution to the holoprotein, and the luminescence activity or pattern can be measured using a luminometer. Luminometers that may be used include commercially available instruments, such as the TD-4000™ (Labo Science) and the Berthold Centro LB 960™ (Berthold Technologies).

In the present specification, "a protein which bonds with a peroxide of coelenterazine or a peroxide of a coelenterazine derivative so as to form a holoprotein" means not only (1) that the protein bonds with a peroxide of coelenterazine or a peroxide of a coelenterazine derivative to form a holoprotein, but also (2) that the protein comes into contact with coelenterazine or a derivative thereof in the presence of oxygen, thereby forming a holoprotein (complex) of the protein with a peroxide of coelenterazine or a peroxide of a coelenterazine derivative.

In the present specification, the term "coelenterazine derivative" refers to a compound having the ability to bond with the protein of the invention so as to form a holoprotein capable of emitting light under the action of calcium ions.

The proteins of the invention are exemplified more specifically by: (a) a protein which has the amino acid sequence of SEQ ID NO: 1, (b) proteins which have an amino acid sequence with, in the amino acid sequence of SEQ ID NO: 1, one or more deleted, substituted, inserted and/or added amino acid, and which possess an activity or ability substantially similar to that of the protein having the amino acid sequence of SEQ ID NO: 1; (c) proteins which include the amino acid sequence of SEQ ID NO: 1, and which possess an activity or ability substantially similar to that of the protein having the amino acid sequence of SEQ ID NO: 1; and (d) proteins which include an amino acid sequence with, in the amino acid sequence of SEQ ID NO: 1, one or more deleted, substituted, inserted and/or added amino acid, and which possess an activity or ability substantially similar to that of the protein having the amino acid sequence of SEQ ID NO: 1.

In the present specification, the range of "one or more" in "amino acid sequence having one or more deleted, substituted, inserted and/or added amino acid" is exemplified by from 1 to 16, 1 to 10, 1 to 9, 1 to 8, 1 to 7, 1 to 6 (from 1 to several), 1 to 5, 1 to 4, 1 to 3, 1 or 2, or 1. A smaller number of deleted, substituted, inserted and/or added amino acids is generally more preferable. Any two or more types of changes from among the above deletions, substitutions, insertions and additions in amino acid residues may occur concurrently. Such proteins may be obtained by using a site-specific mutagenesis technique described in, for example, MOLECULAR CLONING, 3$^{RD}$ ED.; CURRENT PROTOCOLS IN MOLECULAR BIOLOGY; Nuc. Acids. Res., 10, 6487 (1982); Proc. Natl. Acad. Sci. USA, 79, 6409 (1982); Gene, 34, 315 (1985); Nuc. Acids. Res., 13 4431 (1985); or Proc. Natl. Acad. Sci. USA, 82, 488 (1985).

In the amino acid sequence with, in the amino acid sequence of SEQ ID NO: 1, deleted, substituted, inserted and/or added amino acid, it is preferable for at least 5, at least 6, at least 7, at least 8, at least 9, at least 10, at least 11, at least 12, at least 13, at least 14, at least 15, at least 16, at least 17, at least 18, at least 19, at least 20 or at least 21 of amino acids 1, 3, 5, 10, 25, 46, 66, 75, 78, 80, 81, 84, 88, 92, 99, 100, 104, 107, 117, 137, 176 and 177 of the amino acid sequence of SEQ ID NO: 1 to be deleted or substituted. A larger number of amino acids that are not deleted or substituted is generally more preferable.

Specific examples of the protein of the invention include proteins which include the amino acid sequence of SEQ ID NO: 1, proteins which include the amino acid sequence of SEQ ID NO: 3, proteins which include the amino acid sequence of SEQ ID NO: 5, proteins which include the amino acid sequence of SEQ ID NO: 7, proteins which include the amino acid sequence of SEQ ID NO: 9, and proteins which include the amino acid sequence of SEQ ID NO: 11.

Proteins which include the amino acid sequence of SEQ ID NO: 1 are exemplified by the protein having the amino acid sequence of SEQ ID NO: 3, proteins which include the amino acid sequence of SEQ ID NO: 11 are exemplified by the protein having the amino acid sequence of SEQ ID NO: 9 or SEQ ID NO: 7, and proteins which include the amino acid sequence of SEQ ID NO: 9 are exemplified by the protein having the amino acid sequence of SEQ ID NO: 7.

Proteins which include the amino acid sequence of SEQ ID NO: 1 are preferably exemplified by the protein having the amino acid sequence of SEQ ID NO: 1, proteins which include the amino acid sequence of SEQ ID NO: 3 are preferably exemplified by the protein having the amino acid sequence of SEQ ID NO: 3, proteins which include the amino acid sequence of SEQ ID NO: 5 are preferably exemplified by the protein having the amino acid sequence of SEQ ID NO: 5, proteins which include the amino acid sequence of SEQ ID NO: 7 are preferably exemplified by the protein having the amino acid sequence of SEQ ID NO: 7, proteins which include the amino acid sequence of SEQ ID NO: 9 are preferably exemplified by the protein having the amino acid sequence of SEQ ID NO: 9, and proteins which include the amino acid sequence of SEQ ID NO: 11 are preferably exemplified by the protein having the amino acid sequence of SEQ ID NO: 11.

Preferred examples of proteins having an amino acid sequence with, in the amino acid sequence of SEQ ID NO: 1, one or more deleted, substituted, inserted and/or added amino acid include proteins having an amino acid sequence with an alanine to proline substitution at amino acid 75 on the amino acid sequence of SEQ ID NO: 1, proteins having an amino acid sequence with a glutamic acid to lysine substitution at amino acid 88 on the amino acid sequence of SEQ ID NO: 1, and proteins consisting of an amino acid sequence in which two or three of the foregoing amino acids are substituted concurrently (e.g., proteins including an amino acid sequence with an alanine to proline substitution at amino acid 75 and a glutaric acid to lysine substitution at amino acid 88).

Preferred examples of proteins including an amino acid sequence with, in the amino acid sequence of SEQ ID NO: 1, one or more deleted, substituted, inserted and/or added amino acid include proteins which include an amino acid sequence with an alanine to proline substitution at amino acid 75 on the amino acid sequence of SEQ ID NO: 1, proteins which include an amino acid sequence with a glutamic acid to lysine substitution at amino acid 88 on the amino acid sequence of SEQ ID NO: 1, and proteins which include an amino acid sequence in which two or three of the foregoing amino acids are substituted concurrently (e.g., proteins which include an amino acid sequence with an alanine to proline substitution at amino acid 75 and a glutaric acid to lysine substitution at amino acid 88).

Proteins having an activity or ability substantially similar to the protein having the amino acid sequence of SEQ ID NO: 1 are exemplified by proteins which have an amino acid sequence that is at least approximately 90% identical, at least approximately 91% identical, at least approximately 92% identical, at least approximately 93% identical, at least approximately 94% identical, at least approximately 95% identical, at least approximately 96% identical, at least approximately 97% identical, at least approximately 98% identical, or at least approximately 99% identical with the amino acid sequence of SEQ ID NOS: 1, 3, 5, 7, 9 or 11, and which have an activity or ability substantially similar to the protein with the amino acid sequence of SEQ ID NO: 1; and proteins which include an amino acid sequence that is at least approximately 90% identical, at least approximately 91% identical, at least approximately 92% identical, at least approximately 93% identical, at least approximately 94% identical, at least approximately 95% identical, at least approximately 96% identical, at least approximately 97% identical, at least approximately 98% identical, or at least approximately 99% identical with the amino acid sequence of SEQ ID NOS: 1, 3, 5, 7, 9 or 11, and which have an activity or ability substantially similar to the protein with the amino acid sequence of SEQ ID NO: 1. More specific examples include proteins which have an amino acid sequence that is at least approximately 90% identical, at least approximately 91% identical, at least approximately 92% identical, at least approximately 93% identical, at least approximately 94% identical, at least approximately 95% identical, at least approximately 96% identical, at least approximately 97% identical, at least approximately 98% identical, or at least approximately 99% identical with the amino acid sequence of SEQ ID NOS: 1, 3, 5, 7, 9 or 11, and which have the ability to bond with a peroxide of coelenterazine or a peroxide of a coelenterazine derivative so as to form a holoprotein that emits light under the action of a calcium ion; and proteins which include an amino acid sequence that is at least approximately 90% identical, at least approximately 91% identical, at least approximately 92% identical, at least approximately 93% identical, at least approximately 94% identical, at least approximately 95% identical, at least approximately 96% identical, at least approximately 97% identical, at least approximately 98% identical, or at least approximately 99% identical with the amino acid sequence of SEQ ID NOS: 1, 3, 5, 7, 9 or 11, and which have the ability to bond with a peroxide of coelenterazine or a peroxide of a coelenterazine derivative so as to form a holoprotein that emits light under the action of a calcium ion. It is generally preferable for the numerical value indicating the degree of identity to be higher. Identity between amino acid sequences or nucleotide sequences may be determined using a sequencing program such as BLAST (see, for example, Altzchul, S. F. et al., J. Mol. Biol., 215, 403 (1990)) or FASTA (see, for example, Pearson, W. R., Methods in Enzymology, 183, 63 (1990)). When using BLAST or FASTA, the default parameters for the respective programs are employed.

The protein of the invention also includes: (a) proteins which have an amino acid sequence encoded by a polynucleotide that hybridizes under stringent conditions to a polynucleotide having a nucleotide sequence complementary to the nucleotide sequence of SEQ ID NOS: 2, 4, 6, 8, 10 or 12 and which have an activity or ability substantially similar to the protein having the amino acid sequence of SEQ ID NO: 1; and (b) proteins which include an amino acid sequence encoded by a polynucleotide that hybridizes under stringent conditions to a polynucleotide having a nucleotide sequence complementary to the nucleotide sequence of SEQ ID NOS: 2, 4, 6, 8, 10 or 12 and which have an activity or ability substantially similar to the protein having the amino acid sequence of SEQ ID NO: 1. Polynucleotides which hybridize under stringent conditions shall be described subsequently.

The protein of the invention may further include a peptide sequence for purification and/or a secretory signal peptide sequence. Peptide sequences for purification that may be used include peptide sequences employed in the technical field of the invention. Illustrative examples of peptide sequences for purification include histidine tag sequences having a consecutive amino acid sequence of at least four, and preferably at least six, histidine residues; and the amino acid sequence of the glutathione-binding domain in glutathione S-transferase or the amino acid sequence of protein A. "Secretory signal peptide" refers to a peptide region which has the role of transporting a protein or polypeptide that has been bonded to the secretory signal peptide across a cell membrane. Amino acid sequences of such secretory signal peptides and nucleotide sequences encoding such peptides are familiar to, and have been reported in, the technical field of the invention (see, for example, von Heijine, G., Biochim. Biophys. Acra, 947: 307-333 (1988); von Heijine, G., J. Membr. Biol., 115, 195-201 (1990)). More specific examples of secretory signal peptides include the secretory signal peptide from the outer membrane protein A of *E. coli* (OmpA) (Ghrayeb, J. et al., EMBO J., 3, 2437-2442 (1984)) and the secretory signal peptide from cholera toxin obtained from *Vibrio cholerae*.

The method for obtaining the protein of the invention is not subject to any particular limitation. The protein of the invention may be a protein synthesized by chemical synthesis, or a recombinant protein produced by a genetic engineering technique. If the protein of the invention is to be chemically synthesized, synthesis may be carried out by, for example, the Fmoc (fluorenylmethyloxycarbonyl) process or the tBoc (t-butyloxycarbonyl) process. In addition, peptide synthesizers available from, for example, Advanced ChemTech, PerkinElmer, Pharmacia, Protein Technology Instrument, Synthecell-Vega, PerSeptive and Shimadzu Corporation may be used for chemical synthesis. If the protein of the invention is to be produced by a genetic engineering technique, production may be carried out using a conventional genetic recombination technique. More specifically, the protein of the invention may be produced by inserting a polynucleotide (e.g., DNA) encoding the inventive protein into a suitable expression system. The polynucleotide encoding the protein of the invention and expression of the inventive protein with an expression system are described later in the present specification.

By bringing the protein of the invention into contact with the light-emitting substrate coelenterazine or a derivative thereof (e.g., h-coelenterazine, e-coelenterazine, cl-coelenterazine, ch-coelenterazine, hcp-coelenterazine) in the presence of oxygen, a holoprotein composed of the inventive protein and a peroxide of coelenterazine or a peroxide of a coelenterazine derivative can be obtained. "Coelenterazine or a derivative thereof" is referred to below simply as "coelenterazine." In the present specification, the holoprotein composed of the inventive protein and a peroxide of coelenterazine or a peroxide of a coelenterazine derivative is referred to simply as "the holoprotein of the invention" or "CL-II." As used herein, "holoprotein (photoprotein) of the invention" signifies a complex (holoprotein) which includes the protein of the invention (apoprotein) and a peroxide of coelenterazine or a peroxide of a coelenterazine derivative. Examples of the holoprotein of the invention include holoproteins composed of the inventive protein and a peroxide of coelenterazine, and holoproteins composed of the inventive protein and a peroxide of a coelenterazine derivative. Holoproteins composed of the inventive protein and a peroxide of a coelenterazine derivative are exemplified by holoproteins composed of the inventive protein and the peroxide of h-coelenterazine, holoproteins composed of the inventive protein and the peroxide of e-coelenterazine, holoproteins composed of the inventive protein and the peroxide of cl-coelenterazine, holoproteins composed of the inventive protein and the peroxide of ch-coelenterazine, and holoproteins composed of the inventive protein and the peroxide of hcp-coelenterazine. The holoprotein of the invention may be produced from the protein of the invention and coelenterazine in the same way as conventional calcium-binding photoproteins (e.g., aequorin). More specifically, the holoprotein of the invention may be produced by a method in general accordance with the preparation process described in, for example, J. Biol. Chem., 254, 769-780 (1979)). In the presence of oxygen, the holoprotein of the invention exists in the state of a complex of the inventive protein with a peroxide of coelenterazine that arises from coelenterazine and molecular oxygen. When a calcium ion bonds with this complex, light is momentarily emitted, and coelenteramide (an oxide of coelenterazine) and carbon dioxide are formed. This complex (holoprotein of the invention) is referred to herein as the "photoprotein of the invention."

2. Polynucleotide of the Invention

The invention also provides a polynucleotide encoding the above-described protein of the invention. The polynucleotide of the invention may be any having a nucleotide sequence that encodes the protein of the invention, although DNA is preferred. Exemplary DNA includes genomic DNA, genomic DNA libraries, cellular or tissue cDNA, cellular or tissue cDNA libraries, and synthetic DNA. The vectors used in the libraries are not subject to any particular limitation, and may be, for example, bacteriophages, plasmids, cosmids or phagemids. Also, amplification may be carried out directly by a reverse transcription polymerase chain reaction (abbreviated below as "RT-PCR") using total RNA or a mRNA fraction prepared from the above-mentioned cell or tissue.

The polynucleotide of the invention is exemplified by: (a) polynucleotides encoding a protein which has the amino acid sequence of SEQ ID NO: 1; (b) polynucleotides encoding a protein which has an amino acid sequence with, in the amino acid sequence of SEQ ID NO: 1, one or more deleted, substituted, inserted and/or added amino acid, and which possesses a substantially similar activity or ability as the protein having the amino acid sequence of SEQ ID NO: 1; (c) polynucleotides encoding a protein which includes the amino acid sequence of SEQ ID NO: 1, and which possesses a substantially similar activity or ability as the protein having the amino acid sequence of SEQ ID NO: 1; and (d) polynucleotides encoding a protein which includes an amino acid sequence with, in the amino acid sequence of SEQ ID NO: 1, one or more deleted, substituted, inserted and/or added amino acid, and which possesses a substantially similar activity or ability as the protein having the amino acid sequence of SEQ ID NO: 1.

The polynucleotide of the invention is also exemplified by (e) polynucleotides which hybridize under stringent conditions to a polynucleotide having a nucleotide sequence complementary to the nucleotide sequence of SEQ ID NO: 2, and which encode proteins having a substantially similar activity or ability as the protein having the amino acid sequence of SEQ ID NO: 1.

"Polynucleotides (DNA) which hybridize under stringent conditions" refers herein to polynucleotides which are obtained by, for example, colony hybridization, plaque hybridization or Southern hybridization using as the probe all or part of the DNA having a nucleotide sequence complementary to the nucleotide sequence of SEQ ID NOS: 2, 4, 6, 8, 10 or 12 or the DNA encoding the amino acid sequence of SEQ ID NOS: 1, 3, 5, 7, 9 or 11. Specific examples include polynucleotides which can be identified by carrying out hybridization at approximately 65° C. and in the presence of approximately 0.7 to approximately 1.0 mol/L NaCl using a filter on which DNA from a colony or plaque has been immobilized, then washing the filter at approximately 65° C. with an SSC (saline-sodium citrate) solution having a concentration in a range of approximately 0.1 times to approximately 2 times (a 1×SSC solution being composed of approximately 150 mmol/L of sodium chloride and approximately 15 mmol/L of sodium citrate).

Hybridization may be carried out in general accordance with methods described in, for example, Sambrook, J. et al.: MOLECULAR CLONING: A LABORATORY MANUAL, THIRD EDITION (Cold Spring Harbor Laboratory Press, 2001) (abbreviated below as "Molecular Cloning, 3$^{rd}$ Ed."); Ausubel, F. M. et al.: CURRENT PROTOCOLS IN MOLECULAR BIOLOGY, SUPPLEMENTS 1 TO 38 (John Wiley & Sons, 1987-1997); and Glover, D. M. and Hames, B. D.: DNA CLONING 1: CORE TECHNIQUES, A PRACTICAL APPROACH, SECOND EDITION (Oxford University Press, 1995)).

In the present specification, "stringent conditions" may refer to low stringency conditions, moderate stringency conditions and high stringency conditions. "Low stringency conditions" are, for example, approximately 5×SSC, approximately 5×Denhart's solution, approximately 0.5% (w/v) SDS and approximately 50% (v/v) formamide at approximately 32° C. "Moderate stringency conditions" are, for example, approximately 5×SSC, approximately 5×Denhart's solution, approximately 0.5% (w/v) SDS and approximately 50% (v/v) formamide at approximately 42° C. "High stringency conditions" are, for example, approximately 5×SSC, approximately 5×Denhart's solution, approximately 0.5% (w/v) SDS and approximately 50% (v/v) formamide at approximately 50° C. The more stringent the conditions, the higher the complementarity required for double strand formation. Under these conditions, DNA of higher homology is expected to be obtained efficiently at higher temperature, although multiple factors are involved in hybridization stringency, including temperature, probe concentration, probe length, ionic strength, time and salt concentration, and one skilled in the art may appropriately select these factors to realize a similar stringency.

An example of a commercial kit that may be used for hybridization is AlkPhos Direct Labeling Reagents™ (Amersham Pharmacia Biotech). According to the protocol that comes with the kit, following overnight incubation with a labeled probe, the membrane is washed with a primary wash buffer containing approximately 0.1% (w/v) SDS at approximately 55° C., after which the hybridized DNA can be detected.

Other hybridizable DNA include, when calculations are done with a sequencing program such as FASTA or BLAST using the default parameters, DNA that is at least approximately 80%, at least approximately 85%, at least approximately 88%, at least approximately 90%, at least approximately 92%, at least approximately 95%, at least approximately 97%, at least approximately 98%, at least approximately 99%, at least approximately 99.3%, at least approximately 99.5%, at least approximately 99.7%, at least approximately 99.8%, or at least approximately 99.9% identical to DNA encoding the amino acid sequence of SEQ ID NOS: 1, 3, 5, 7, 9 or 11. The identity of an amino acid sequence or a nucleotide sequence can be determined using the above-described method.

A polynucleotide encoding a protein having, with respect to a given amino acid sequence, one or more deleted, substituted, inserted and/or added amino acid, may be obtained using a site-specific mutagenesis technique (see, for example, Gotoh, T. et al., Gene, 152, 271-275 (1995); Zoller, M. J. and Smith, M., Methods Enzymol., 100, 468-500 (1983); Kramer, W. et al., Nucleic Acids Res., 12, 9441-9456 (1984); Kramer, W. and Fritz, H. J., Methods Enzymol., 154, 350-367 (1987); Kunkel, T. A., Proc. Natl. Acad. Sci. USA, 82, 488-492 (1985); Kunkel, Methods Enzymol., 85, 2763-2766 (1988)), and methods employing amber mutation (see, for example, the gapped duplex method in Nucleic Acids Res., 12, 9441-9456 (1984)).

Alternatively, a mutation may be introduced onto the polynucleotide by means of a polymerase chain reaction (PCR) using a set of primers bearing on the respective 5' ends a sequence in which the target mutation (deletion, addition, substitution and/or insertion) has been introduced (see, for example, Ho, S. N. et al., Gene, 77, 51 (1989)).

Also, a polynucleotide encoding a protein partial fragment, which is one type of deletion variant, may be obtained by using as the primers an oligonucleotide having a sequence which matches the nucleotide sequence at the 5' end of the region of the protein-encoding polynucleotide that codes for the partial fragment to be produced and an oligonucleotide having a sequence complementary to the nucleotide sequence at the 3' end thereof, and carrying out a PCR in which the polynucleotide encoding the protein serves as the template.

Illustrative examples of the polynucleotide of the invention include polynucleotides encoding proteins which include the amino acid sequence of SEQ ID NO: 1, polynucleotides encoding proteins which include the amino acid sequence of SEQ ID NO: 3, polynucleotides encoding proteins which include the amino acid sequence of SEQ ID NO: 5, polynucleotides encoding proteins which include the amino acid sequence of SEQ ID NO: 7, polynucleotides encoding proteins which include the amino acid sequence of SEQ ID NO: 9, and polynucleotides encoding proteins which include the amino acid sequence of SEQ ID NO: 11.

Polynucleotides encoding proteins which include the amino acid sequence of SEQ ID NO: 1 are exemplified by polynucleotides which include the nucleotide sequence of SEQ ID NO: 2. Polynucleotides encoding proteins which include the amino acid sequence of SEQ ID NO: 3 are exemplified by polynucleotides which include the nucleotide sequence of SEQ ID NO: 4. Polynucleotides encoding proteins which include the amino acid sequence of SEQ ID NO: 5 are exemplified by polynucleotides which include the nucleotide sequence of SEQ ID NO: 6. Polynucleotides encoding proteins which include the amino acid sequence of SEQ ID NO: 7 are exemplified by polynucleotides which include the nucleotide sequence of SEQ ID NO: 8. Polynucleotides encoding proteins which include the amino acid sequence of SEQ ID NO: 9 are exemplified by polynucleotides which include the nucleotide sequence of SEQ ID NO: 10. Polynucleotides encoding proteins which include the amino acid sequence of SEQ ID NO: 11 are exemplified by polynucleotides which include the nucleotide sequence of SEQ ID NO: 12.

The polynucleotide of the invention may include a polynucleotide encoding a peptide sequence for purification and/or a polynucleotide encoding a secretory signal peptide. A polynucleotide which includes a nucleotide sequence encoding a peptide sequence for purification and is used in the technical field of the invention may be employed as the polynucleotide encoding a peptide sequence for purification. Examples of peptide sequences for purification include those mentioned above. A polynucleotide which includes a nucleotide sequence encoding a secretory signal peptide and is used in the technical field of the Invention may be employed as the polynucleotide encoding a secretory signal peptide. Examples of secretory signal peptides include those mentioned above.

3. Recombinant Vectors and Transformants of the Invention

The invention further provides a recombinant vector and a transformant which include the above-described polynucleotide of the invention.

Construction of Recombinant Vector

The recombinant vector of the invention may be obtained by ligating (inserting) the polynucleotide (DNA) of the invention to a suitable vector. More specifically, the recombinant vector may be obtained by cleaving purified polynucleotide (DNA) with a suitable restriction enzyme, then inserting the cleaved polynucleotide to a restriction enzyme site or multicloning site on a suitable vector, and ligating the polynucleotide to the vector. The vector for inserting the inventive polynucleotide is not subject to any particular limitation, provided it is capable of replication in the host. Vectors that may be used for this purpose include plasmids, bacteriophages, and animal viruses. Illustrative examples of suitable plasmids include plasmids from *E. coli* (e.g., pBR322, pBR325, pUC118 and pUC119), plasmids from *Bacillus subtilis* (e.g., pUB110 and pTP5), and plasmids from yeast (e.g., YEp13, YEp24 and YCp50). An example of a suitable bacteriophage is the λ phage. Examples of suitable animal viruses include retroviruses, vaccinia viruses and insect viruses (e.g., baculoviruses).

The polynucleotide of the invention is generally ligated downstream from the promoter in a suitable vector in such a way as to be expressible. For example, if the host during transformation is an animal cell, preferred promoters include promoters from SV40, retrovirus promoters, metallothionein promoters, heat shock promoters, cytomegalovirus promoters and the SRα promoter. If the host is a genus *Escherichia* organism, preferred promoters include the Trp promoter, the T7 promoter, the lac promoter, the recA promoter, the λPL promoter and the lpp promoter. If the host is a genus *Bacillus* organism, preferred promoters include the SPO1 promoter, the SPO2 promoter and the penP promoter. If the host is a yeast, preferred promoters include the PHO5 promoter, the PGK promoter, the GAP promoter, the ADH1 promoter and the GAL promoter. If the host is an insect cell, preferred promoters include the polyhedrin promoter and the P10 promoter.

In addition to the above, the recombinant vector used in the invention may contain, if desired, an enhancer, a splicing signal, a poly(A) addition signal, a ribosome binding sequence (SD sequence), a selective marker and the like. Illustrative examples of selective markers include the dihydrofolate reductase gene, the ampicillin resistance gene and the neomycin resistance gene.

(2) Preparation of Transformant

The transformant can be created by introducing into a suitable host the recombinant vector, obtained as described above, which contains the polynucleotide of the invention (i.e., a polynucleotide encoding the protein of the invention). The host is not subject to any particular limitation, provided it is capable of expressing the polynucleotide (DNA) of the invention. Examples include bacteria of the genera *Escherichia, Bacillus, Pseudomonas* and *Rhizobium*, yeasts, animal cells and insect cells. Bacteria of the genus *Escherichia* include *E. coli*. Bacteria of the genus *Bacilllus* include *B. subtilis*. Bacteria of the genus *Pseudomonas* include *P. putida*. Bacteria of the genus *Rhizobium* include *R. meliloti*. Yeasts include *Saccharomyces cerevisia* and *Schizosaccharomyces pombe*. Animal cells include COS cells and CHO cells. Insect cells include Sf9 and Sf21.

Introduction of the recombinant vector into the host and transformation thereby may be carried out by any of various commonly used methods. Examples of suitable methods for introducing the recombinant vector into the host cell include the calcium phosphate method (Virology, 52, 456-457 (1973)), lipofection (Proc. Natl. Acad. Sci. USA, 84, 7413 (1987)), and electroporation (EMBO J., 1, 841-845 (1982)). Examples of methods for transforming genus *Escherichia* bacteria include the methods described in Proc. Natl. Acad. Sci. USA, 69, 2110 (1972), and Gene, 17, 107 (1982). Methods for transforming genus *Bacillus* bacteria include the methods described in Molecular & General Genetics, 168, 111 (1979). Methods for transforming yeasts include the methods described in Proc. Natl. Acad. Sci. USA, 75, 1929 (1978). Methods for transforming animal cells include the methods described in Virology, 52, 456 (1973). Methods for transforming insect cells include the methods described in Bio/Technology, 6, 47-55 (1988). A transformant created by transformation with a recombinant vector containing the polynucleotide which codes for the protein of the invention (i.e., the polynucleotide of the invention) can be obtained in this way.

4. Production of Inventive Protein

The invention also provides a method for producing the protein of the invention, which method includes the step of culturing the above-described transformant so as to induce the production thereby of the invention. The protein of the invention may be produced by culturing the transformant under conditions that allow the polynucleotide (DNA) encoding the inventive protein to be expressed, thereby inducing formation and accumulation of the inventive protein, then isolating and purifying the protein.

Culturing the Transformant:

The transformant of the invention may be cultivated by an conventional method used for culturing hosts. In such cultivation, the protein of the invention is formed by the transformant and accumulates within the transformant or the culture broth.

The medium for culturing the transformant using a genus *Escherichia* or *Bacillus* bacterium as the host may be a natural medium or a synthetic medium, provided it is a medium which contains the carbon sources, nitrogen sources, inorganic salts and other nutrients essential for growth of the transformant, and in which the transformant can be efficiently grown. Examples of carbon sources that may be used include carbohydrates such as glucose, fructose, sucrose and starch; organic acids such as acetic acid and propionic acid; and alcohols such as ethanol and propanol. Examples of nitrogen sources that may be used include ammonia, ammonium salts of inorganic or organic acids, such as ammonium chloride, ammonium sulfate, ammonium acetate and ammonium phosphate, other nitrogen-containing compounds, and also peptone, meat extract and corn steep liquor. Examples of inorganic salts include monobasic potassium phosphate, dibasic potassium phosphate, magnesium phosphate, magnesium sulfate, sodium chloride, ferrous sulfate, manganese sulfate, copper sulfate and calcium carbonate. If necessary, antibiotics such as ampicillin or tetracycline may be added to the medium during culturing. If the transformant to be cultured has been obtained by transformation with an expression vector using an inducible promoter as the promoter, if necessary, the inducer may also be added to the medium. For example, isopropyl-β-D-thiogalactopyranoside (IPTG) may be added to the medium when culturing a transformant obtained by transformation with an expression vector using a Lac promoter, and indoleacrylic acid (IAA) may be added to the medium when culturing a transformant obtained by transformation with an expression vector using a trp promoter.

When the host is a bacterium of the genus *Escherichia*, incubation is generally carried out at approximately 15 to approximately 43° C. for approximately 3 to approximately 24 hours. If necessary, aeration and stirring may be applied. When the host is a bacterium of the genus *Bacillus*, incubation is generally carried out at approximately 30 to approximately 40° C. for approximately 6 to approximately 24 hours. If necessary, aeration and stirring may be applied.

Media for culturing the transformant when the host is a yeast are exemplified by Burkholder's minimal medium (Proc. Natl. Acad. Sci. USA, 77, 4505 (1980)) and an SD medium containing approximately 0.5% (w/v) casamino acids (Proc. Natl. Acad. Sci. USA, 81, 5330 (1984)). The pH of the medium is preferably adjusted to approximately 5 to approximately 8. Culturing is generally carried out at approximately 20 to approximately 35° C. for approximately 24 to approximately 72 hours. If necessary, aeration and stirring may be applied.

Media for culturing the transformant when the host is an animal cell are exemplified by MEM media containing approximately 5 to approximately 20% (v/v) fetal calf serum (Science, 122, 501 (1952)) and DMEM media (Virology, 8, 396 (1959)). The pH of the medium is preferably adjusted to approximately 6 to approximately 8. Culturing is generally carried out at approximately 30 to approximately 40° C. for approximately 15 to approximately 60 hours. If necessary, aeration and stirring may be applied.

Media for culturing the transformant when the host is an insect cell are exemplified by Grace's insect medium (Nature, 195, 788 (1962)) to which additives such as approximately 10% (v/v) immobilized bovine serum have been suitably added. The pH of the medium is preferably adjusted to approximately 6.2 to approximately 6.4. Culturing is generally carried out at approximately 27° C. for approximately 3 to approximately 5 hours. If necessary, aeration and stirring may be applied.

Isolation and Purification of Inventive Protein:

The protein of the invention may be obtained by isolating and purifying the inventive protein from the above-described culture. As used herein, "culture" refers to any one of the following: a culture broth, cultured bacteria, cultured cells, and the products obtained by disrupting cultured bacteria or cultured cells. Conventional methods may be used to isolate and purify the protein of the invention.

Specifically, when the protein of the invention accumulates within cultured bacteria or within cultured cells, following the completion of cultivation, an extract of the target protein may be obtained by a conventional method such as centrifugation or filtration after using a conventional technique (e.g., ultrasound, lysozymes, freezing and thawing) to disrupt the bacteria or cells. When the inventive protein accumulates in the periplasmic space, following the completion of cultivation, an extract containing the inventive protein may be obtained by a conventional method such as osmotic shock. When the inventive protein accumulates in the culture broth, following the completion of cultivation, a culture supernatant containing the inventive protein may be obtained by using a conventional method such as centrifugation or filtration to separate the culture supernatant from the bacteria or cells.

Purification of the inventive protein present in the extract or culture supernatant obtained as described above may be carried out by a conventional method of separation and purification. Examples of separation and purification methods that may be used include ammonium sulfate precipitation, gel filtration chromatography, ion-exchange chromatography, affinity chromatography, reversed-phase high-performance liquid chromatography, dialysis, and ultrafiltration, as well as suitable combinations thereof. If the inventive protein includes the above-described peptide sequence for purification, it is preferable to carry out purification using the same. Specifically, if the inventive protein contains a histidine tagging sequence, use may be made of nickel chelate affinity chromatography; if the inventive protein contains the glutathione-binding domain of S-transferase, use may be made of affinity chromatography using a glutathione-binding gel; if the inventive protein contains the amino acid sequence of Protein A, use may be made of antibody affinity chromatography.

The holoprotein (photoprotein) of the invention which emits light in a degree that depends on the calcium ion concentration may be prepared by incubating at a low temperature the purified apoprotein of the invention together with the light-emitting substrate coelenterazine or a derivative thereof in the presence of a reducing agent (e.g., mercaptoethanol, dithiothreitol) and oxygen.

5. Uses of the Inventive Protein

Detection and Assay of Calcium Ions:

As noted above, a holoprotein (photoprotein) is a protein which can be formed by the non-covalent bonding of a protein of the invention (apoprotein) with a peroxide of coelenterazine or a peroxide of coelenterazine derivative formed from coelenterazine or a derivative thereof with molecular oxygen, and which emits light through the action of a calcium ion. The protein of the invention and the holoprotein of the invention may be used for detecting and assaying calcium ions.

When the protein of the invention is employed to detect or assay calcium ions, a holoprotein composed of the inventive protein (apoprotein) and a peroxide of coelenterazine or a peroxide of a coelenterazine derivative is used. The holoprotein may be produced in accordance with the above-described method. The detection or assay of calcium ions may be carried out by adding the sample solution directly to a solution of the holoprotein and measuring the luminescence that is generated. Alternatively, the detection or assay of calcium ions may be carried out by adding a solution of the holoprotein to the sample solution and measuring the luminescence that is generated. Another possibility is to first bring an aqueous solution of the inventive protein (apoprotein) into contact with coelenterazine or a derivative therein (e.g., h-coelenterazine, e-coelenterazine, cl-coelenterazine, ch-coelenterazine, hcp-coelenterazine) so as to form the holoprotein, then use the holoprotein thus formed by adding it to a measurement system for detecting or assaying calcium ions. A further possibility is to bring the inventive protein (apoprotein) into contact with coelenterazine or a derivative thereof within the measurement system so as to form a holoprotein composed of the inventive protein and a peroxide of coelenterazine or a peroxide of a coelenterazine derivative. The holoprotein thus formed is a complex (photoprotein) of the inventive protein (apoprotein) and a peroxide of coelenterazine or a peroxide of a coelenterazine derivative; the complex (i.e., the inventive holoprotein) luminesces to a degree that depends on the calcium ion concentration. The (apoprotein) of the invention or the holoprotein of the invention may thus be used to detect calcium ions. As noted above, the detection of calcium ions may be carried out by adding the sample solution directly to the holoprotein solution and measuring the luminescence that is generated. Alternatively, detection of the calcium ions may be carried out by measuring the luminescence that is generated when the holoprotein solution is added to the sample solution.

The detection or assay of calcium ions may be carried out by using a luminometer to measure the light emitted by the holoprotein of the invention owing to the action of calcium ions. Luminometers that may be used include commercially available instruments, such as the Centro LB 960™ (Berthold Technologies). Quantitative determination of the calcium ion concentration can be carried out by first preparing a luminescence standard curve for known calcium ion concentrations using the holoprotein.

By constructing a holoprotein composed of the inventive protein and a peroxide of coelenterazine or a peroxide of a coelenterazine derivative, and directly introducing the holoprotein into the cell using a technique such as microinjection, the inventive protein may be used to detect intracellular changes in the calcium ion concentration under physiological conditions.

Other than introduction into a cell by a technique such as microinjection, the protein of the invention may be formed intracellularly by the intracellular expression of an apoprotein gene (a polynucleotide encoding the protein of the invention). In addition, a holoprotein may be formed by furnishing to the inventive protein thus formed (apoprotein) a coelenterazine or derivative thereof from outside the cell.

Using the inventive holoprotein that has been introduced into or formed within the cell in this way, changes in the intracellular calcium ion concentration in response to external stimuli (e.g., stimuli by a drug which acts on a receptor) can be measured.

Use as a Reporter Protein:

The protein of the invention may be used as a reporter protein to measure the transcription activity of promoters and the like. The polynucleotide encoding the inventive protein (i.e., the polynucleotide of the invention) is fused with the target promoter or some other expression control sequence (e.g., an enhancer) to construct a vector. By introducing the vector into the host cell and detecting the luminescence arising from the inventive protein (i.e., the luminescence by the holoprotein of the invention), the activity of the target promoter or some other expression control sequence may be measured.

As mentioned above, the polynucleotide of the invention may be used as a reporter gene.

Use as Marker for Detection by Luminescence

The protein of the invention may be employed as a marker for detection by luminescence. The detection marker of the invention may be employed to detect a target substance in, for example, an immunoassay or hybridization assay. The holoprotein of the invention may be employed by using a commonly used method such as chemical modification to cause it bond with a target protein or a target nuclei acid. Detection methods using such detection markers may be carried out by a conventional method. The detection marker of the invention may be utilized to measure the distribution of a target protein by expressing the marker as a fused protein with the target protein, then inserting the fused protein into a cell by a suitable technique such as microinjection. Measurement of the distribution of such a target protein may be carried out using a method of detection such as luminescent imaging. Aside from insertion into a cell by a technique such as microinjection, it is also possible to use the protein of the invention by expressing it within a cell.

Materials for Recreational Products:

A complex composed of the inventive protein and a peroxide of coelenterazine or a peroxide of a coelenterazine derivative (which complex is the holoprotein of the invention) emits light simply by bonding with a trace amount of calcium ions. Light emission by the complex (the inventive holoprotein) exhibits a luminescence intensity at least five times greater than that of conventional photoproteins. Therefore, the protein and holoprotein of the invention may be suitably employed as a luminescent base material for use in recreational product-related materials. Examples of recreational products include luminescent soap balls, luminescent ice, luminescent candy and luminescent artists' colors. Recreational products of the invention may be produced by conventional methods.

6. Kit According to the Invention

The invention also provides a kit which includes any of the following: proteins of the invention, holoproteins of the invention, polynucleotides of the invention, recombinant vectors of the invention, and transformants of the invention. The inventive kit may additionally include coelenterazine or a derivative thereof, and may be produced with the use of conventional materials and methods. The inventive kits may also contain sample tubes, plates, instructions for the user, solutions, buffers, reagents, and either samples suitable for standardization or control samples.

The inventive kit may be employed for the above-described detection or assay of the calcium ions, for measurement using a reporter protein or a reporter gene, or as a fluorescent marker.

Where no particular explanation is given in the preferred embodiments for working the invention or the examples of the invention, use will typically be made of the methods described in standard collections of protocols, such as J. Sambrook, E. F. Fritsch & T. Maniatis (Eds.), MOLECULAR CLONING, A LABORATORY MANUAL ($3^{RD}$ EDITION) (Cold Spring Harbor, N.Y., Cold Spring Harbor Press, 2001) and F. M. Ausubel, R. Brent, R. E. Kingston, D. D. Moore, J. G. Seidman, J. A. Smith, K. Struhl (Eds.), CURRENT PROTOCOLS IN MOLECULAR BIOLOGY (John Wiley & Sons, Ltd.), or modifications or variations thereof. When commercially available reagent kits and measurement equipment are used, unless noted otherwise herein, the protocols provided therewith will typically be followed.

The objects, features, advantages and ideas of the invention will be apparent to those skilled in the art from the description provided in the specification, and the invention will be readily practicable by those skilled in the art on the basis of the description appearing herein. The Description of the Preferred Embodiments and the Examples which show preferred modes for practicing the invention are included for the purpose of illustration and explanation, and are not intended to limit the scope of the claims. It will be apparent to those skilled in the art that various modifications may be made in how the invention is practiced based on described aspects in the specification without departing from the spirit and scope of the invention disclosed herein.

Sequence numbers in the Sequence Listing of the present specification indicate the following sequences:

SEQ ID NO: 1 shows the amino acid sequence of the apoCL-II protein encoded by the DNA which codes for apoCL-II and which has been inserted into the apoCL-II protein expression vector piP-H-CLII constructed in Example 5. This amino acid sequence corresponds to amino acids 4 to 189 of SEQ ID NO: 3 or amino acids 38 to 223 of SEQ ID NO: 5.

SEQ ID NO: 2 shows the nucleotide sequence of DNA which codes for apoCL-II and which has been inserted into the apoCL-II protein expression vector piP-H-CLII constructed in Example 5. This nucleotide sequence corresponds to nucleotides 10 to 567 of SEQ ID NO: 4 or nucleotides 112 to 669 of SEQ ID NO: 6.

SEQ ID NO: 3 shows the sequence of amino acids 35 to 223 inferred from the nucleotide sequence of the CL-II group cDNA clone pCL31 determined in Example 3. This amino acid sequence corresponds to amino acids 35 to 223 of SEQ ID NO: 5.

SEQ ID NO: 4 shows the nucleotide sequence of DNA which codes for the protein represented by SEQ ID NO: 3. This nucleotide sequence corresponds to nucleotides 103 to 669 of SEQ ID NO: 6.

SEQ ID NO: 5 shows the amino acid sequence inferred from the nucleotide sequence of the CL-II group cDNA clone pCL31 determined in Example 3.

SEQ ID NO: 6 shows the nucleotide sequence of the CL-II group cDNA clone pCL31 determined in Example 3.

SEQ ID NO: 7 shows the amino acid sequence inferred from the nucleotide sequence of the CL-II group cDNA clone pCL61R determined in Example 3.

SEQ ID NO: 8 shows the nucleotide sequence of the CL-II group cDNA clone pCL61R determined in Example 3.

SEQ ID NO: 9 shows the sequence of amino acids 47 to 235 in SEQ ID NO: 7.

SEQ ID NO: 10 shows the sequence of nucleotides 139 to 705 in SEQ ID NO: 8.

SEQ ID NO: 11 shows the sequence of amino acids 50 to 235 in SEQ ID NO: 7.

SEQ ID NO: 12 shows the sequence of nucleotides 148 to 705 in SEQ ID NO: 8.

SEQ ID NO: 13 shows the amino acid sequence inferred from the nucleotide sequence of the CL-II group cDNA clone pCL21 determined in Example 3.

SEQ ID NO: 14 shows the nucleotide sequence of the CL-II group cDNA clone pCL21 determined in Example 3.

SEQ ID NO: 15 shows the amino acid sequence inferred from the nucleotide sequence of the CL-I group cDNA clone pCL11 determined in Example 3.

SEQ ID NO: 16 shows the nucleotide sequence of the CL-I group cDNA clone pCL11 determined in Example 3.

SEQ ID NO: 17 shows the amino acid sequence inferred from the nucleotide sequence of the CL-I group cDNA clone pCL41 determined in Example 3.

SEQ ID NO: 18 shows the nucleotide sequence of the CL-I group cDNA clone pCL41 determined in Example 3.

SEQ ID NO: 19 shows the amino acid sequence inferred from the nucleotide sequence of the CL-I group cDNA clone pCL51R determined in Example 3.

SEQ ID NO: 20 shows the nucleotide sequence of the CL-I group cDNA clone pCL51R determined in Example 3.

SEQ ID NO: 21 shows the amino acid sequence inferred from the nucleotide sequence of the CL-I group cDNA clone pCL81 determined in Example 3.

SEQ ID NO: 22 shows the nucleotide sequence of the CL-I group cDNA clone pCL81 determined in Example 3.

SEQ ID NO: 23 shows the amino acid sequence of the protein encoded by the apoCL-II protein expression vector piP-H-CLII constructed in Example 5. This sequence corresponds to the amino acid sequence of the protein obtained by bonding the OmpA signal peptide, a histidine tag and a peptide from the nucleotide sequence at the multicloning site of the expression vector piP-H-CLII to the N-terminus of the protein having the amino acid sequence of SEQ ID NO: 1.

SEQ ID NO: 24 shows a nucleotide sequence coding for a protein in the apoCL-II protein expression vector piP-H-CLII constructed in Example 5.

SEQ ID NO: 25 shows the amino acid sequence for apoCL-I protein encoded by the DNA which encodes apoCL-I and was inserted into the apoCL-I protein expression vector piP-H-CLI constructed in Reference Example 1. This amino acid sequence corresponds to the sequence of amino acids 26 to 214 in SEQ ID NO: 17.

SEQ ID NO: 26 shows the nucleotide sequence of DNA which codes for apoCL-I and was inserted in the apoCL-I protein expression vector piP-H-CI constructed in Reference Example 1.

SEQ ID NO: 27 shows the amino acid sequence of the protein encoded by the apoCL-I protein expression vector piP-H-CLI constructed in Reference Example 1. This sequence corresponds to the amino acid sequence of the protein obtained by bonding the OmpA signal peptide, a histidine tag and a peptide from the nucleotide sequence at the multicloning site of the expression vector piP-H-CLI to the N-terminus of the protein having the amino acid sequence of SEQ ID NO: 25.

SEQ ID NO: 28 shows a nucleotide sequence coding for a protein in the apoCL-I protein expression vector piP-H-CLI constructed in Reference Example 1.

SEQ ID NO: 29 shows the sequence of amino acids 1 to 34 in SEQ ID NO: 5.

SEQ ID NO: 30 shows the sequence of nucleotides 1 to 102 in SEQ ID NO: 6.

SEQ ID NO: 31 shows the sequence of amino acids 1 to 46 in SEQ ID NO: 7.

SEQ ID NO: 32 shows the sequence of nucleotides 1 to 138 in SEQ ID NO: 8.

SEQ ID NO: 33 shows the nucleotide sequence of the oligonucleotide which encodes the sequence of six histidines used in Example 4.

SEQ ID NO: 34 shows the nucleotide sequence of the oligonucleotide which encodes the sequence of six histidines used in Example 4.

SEQ ID NO: 35 shows the nucleotide sequence of the primer used in Example 5.

SEQ ID NO: 36 shows the nucleotide sequence of the primer used in Example 5.

SEQ ID NO: 37 shows the nucleotide sequence of the primer used in Reference Example 1.

SEQ ID NO: 38 shows the nucleotide sequence of the primer used in Reference Example 1.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

EXAMPLES

Examples are given below to more fully illustrate the invention, and should not be construed as limiting the invention.

Example 1

Gene Cloning Method

The cDNA of the luminescent jellyfish Clytia gregarium was isolated as described in a published reference by the inventors (Inouye, S, and Tsuji, F. I., FEBS Lett., 315, 343-346 (1993)). This involved extracting the total RNA from C. gregarium by the guanidine isocyanate method, carrying out polyA$^+$ purification with an oligo dT gel, and creating the cDNA with reverse transcriptase. The resulting cDNA was inserted in a phage vector, following which a cDNA library was constructed by in vitro packaging. Isolation of the clytin cDNA from the cDNA library was carried out by screening with the HIndIII-BamHI fragment of the cDNA clone pAQ440 of aequorin (Inouye et al., Proc. Natl. Acad. Sci. USA, 82, 3154-3158 (1985)) as the probe and using the plaque hybridization method in accordance with the foregoing literature reference.

Example 2

Isolation of cDNA Clone

Seven positive clones were obtained from the cDNA library in accordance with Example 1. Restriction enzyme maps were constructed using EcoRI (E), BamHI (B), HindIII (H) and StyI (S). As shown in FIG. 1, it became apparent that the results can be divided into two groups. The respective groups were named Clytin-I (also abbreviated below as "CL-I") and Clytin-II (also abbreviated below as "CL-II"). CL-I corresponds to a group that has already been reported in Inouye, S. and Tsuji, F. I., FEBS Lett., 315, 343-346 (1993).

Example 3

Determination of Nucleotide Sequence and Determination of Primary Structure

The nucleotide sequences of the CL-I group cDNA clones pCL11, pCL41, pCL51R and pCL81 and the CL-II group cDNA clones pCL21, pCL31 and pCL61R obtained in Examples 1 and 2 were determined. On comparing the amino acid sequences inferred from the nucleotide sequences, as can be seen in FIG. 2, the CL-I and CL-II amino acid sequences exhibited a high homology. Yet, as shown in the restriction enzyme maps, separation into the two groups was appropriate.

The homology between the amino acid sequence of CL-II (pCL31) and the amino acid sequences of the earlier reported calcium-binding photoproteins clytin (CL-I, Clytin-I), aequorin, mitrocomin and obelin was investigated. Comparisons of the homology were carried out on all of the calcium-binding photoproteins shown in Table 1 below, based on the sequence of amino acid residues 1 to 189 which is the active region of the photoprotein aequorin that has been acquired from the NCBI database and closely analyzed.

TABLE 1

List of Photoproteins for Which the Homology Was Compared

| Photoprotein | Plasmid Name | Scientific Name | GenBank Acc. No. |
| --- | --- | --- | --- |
| Clytin | pCL41 | C. gregarium | L13247 |
| Aequorin | pAQ440 | A. victoria | L29571 |
| Mitrocomin | pMI-17 | M. cellularia | L31623 |
| Obelin | pET19-OG | O. geniculata | AF394688 |
| Obelin | pOL101 | O. longissima | U07128 |

The results are shown in Table 2. The photoprotein having the highest homology with CL-II was CL-I, followed in turn by obelin, aequorin, and mitrocomin.

TABLE 2

Comparison of Photoprotein Homologies

|  | CL-I (pCL41) | CL-II (pCL31) | Aequorin (pAQ440) | Mitrocomin (pMI-17) | Obelin (pET19-OG) | Obelin (pOL101) |
| --- | --- | --- | --- | --- | --- | --- |
| CL-I (pCL41) | * | 88.4 | 64.0 | 64.5 | 77.8 | 77.8 |
| CL-II (pCL31) |  | * | 61.9 | 60.8 | 76.2 | 76.7 |
| Aequorin (pAQ440) |  |  | * | 68.8 | 65.6 | 68.8 |
| Mitrocomin (pMI-17) |  |  |  | * | 64.6 | 64.0 |
| Obelin (pET19-OG) |  |  |  |  | * | 86.2 |

Example 4

Construction of Basic Vector piP-H6-M (11)

The basic vector piP-H6-M(11) which, when the target protein has been expressed using E. coli as the host, is capable of secretion into the periplasm of the E. coli, and which is capable of expressing a protein having six histidines at the amino-terminal end was constructed by the following procedure.

Creation of piP-HE

The apoaequorin secretory expression vector piP-HE described in Japanese Patent Application Laid-open No. H1-132397 was used as the starting vector. The following procedure was used to create piP-HE.

Construction of piQ8-HE

The EcoRI-HindIII portion of the high-copy cloning vector pUC8 was digested by the respective restriction enzymes, following which the EcoRI-HindIII fragment of aequorin cDNA obtained from the cDNA cloning gene pAQ440 prepared by the method described in Japanese Patent Laid-open No. S61-135586 was subcloned to this portion, thereby creating piQ8-HE.

(2) Construction of piP-HE piQ8-HE was digested by ScaI-HindIII, following which a ScaI-HindIII fragment which contained the lipoprotein promoter (lpp), the lac operator and the OmpA gene and which had been cut from pIN-III 113 OmpA-1 was inserted here, thereby creating the expression vector piP-HE.

Construction of piP(His6)HE piP-HEΔ2E obtained from piP-HE by removing the EcoRI site on the carboxy-terminal end was used. Oligonucleotides encoding sequences of six histidines (Eco-His6-Hind Linker: 5'-AAT-TCC-CAC-CAT-CAC-CAT-CAC-CAT-GGT 3' (SEQ ID NO: 33), and Eco-H is 6-Hind Linker: 5'-AG-CTT-ACC-ATG-GTG-ATG-GTG-GG 3' (SEQ ID NO: 34)) were inserted at the HindIII-EcoRI site on piP-HEΔ2E, thereby constructing piP(His6)HE.

Construction of piP-H6-M(11)

In addition, a chemically synthesized linker having multi-cloning sites (NcoI/HindIII/NdeI/SacI/KpnI/XhoI/BamHI/EcoRI/SalI/PstI/XbaI) (available from Operon) was inserted at the HindIII-BamHI site on the piP(His6)HE vector, thereby constructing piP-H6-M(11). The basic vector piP-H6-M(11) was controlled by the lipoprotein promoter and the lactose operator in E. coli, and had an OmpA sequence for secretion, a sequence composed of six histidines for purification via the chelate gel method, and various multicloning sites (EcoRI/NcoI/HindIII/NdeI/SacI/KpnI/XhoI/BamHI/EcoRI/SalI/PstI/XbaI/BamHI) (FIG. 3(a)).

Example 5

Construction of ApoCL-II Protein Expression Vector

The gene DNA fragment coding for CL-II from the cDNA clone pCL31 obtained in Example 2 was prepared using the PCR method. The CL-II protein expression vector was constructed by inserting this DNA fragment at the restriction enzyme SacI/XhoI site of the expression vector piP-H-M(11) obtained in Example 4. That is, a polymerase chain reaction (cycle conditions: 25 cycles, each consisting of 1 minute at 94° C., 1 minute at 50° C. and 1 minute at 72° C.) was carried out by means of a PCR kit (Nippon Gene) with pCL31 as the template and using the PCR primer pair: CLII-N-EL-SacI (5' ggcGAGCTCGATCCTGATTTTGCAAAT 3') (SEQ ID NO: 35) and CLI-C-XhoI (5' cggCTCGAGTTAACCAA-CAAAATTGCCGTA 3') (SEQ ID NO: 36). The resulting fragment was purified with a PCR purification kit (Qiagen) and digested with the restriction enzyme SacI/XhoI, then inserted at the restriction enzyme SacI/XhoI site of piP-H-M (11), thereby constructing the expression vector piP-H-CLII (FIG. 3B). Verification of the insert DNA was carried out by using a DNA sequencer (available from ABI) to determine the nucleotide sequence.

Example 6

Purification of CL-II

Expression of Recombinant ApoCL-II in E. coli

The CL-II gene expression vector piP-H-CL-II obtained in Example 5 was used to express recombinant CL-II in E. coli. The vector was inserted into the E. coli strain WA802 by a conventional method, and the resulting transformed strain was cultured overnight at 25° C., following which it was inoculated onto 10 mL of LB liquid medium (composed of 10 g of bactotryptone, 5 g of yeast extract and 5 g of sodium chloride per liter of water; pH 7.2) containing ampicillin (50

μg/mL) and additionally cultured at 37° C. for 18 hours. The culture was then added to 5 vessels holding 400 mL each of fresh LB liquid medium (total amount, 2 liters) and cultivated at 37° C. for 18 hours. Following cultivation, the bacterial cells were collected by centrifugation (5 minutes at 5,000 rpm), yielding a starting material for CL-II extraction.

(2) apoCL-II Extraction and Purification from Cultured Bacteria

After being harvested, the cultured bacteria were suspended in 200 mL of 50 mM Tris-HCl (pH 7.6), and subjected three times to 2 minutes each of ultrasonic disruption under ice cooling (Branson, Sonifier model cycle 250). The resulting cell ultrasonicate was then centrifuged at 10,000 rpm (12,300×g) and 4° C. for 20 minutes. The resulting soluble fraction was applied to a nickel chelate column (Amersham Bioscience; column size: 1.5 cm (dia)×5 cm), and the apoCL-II was desorbed. The column was then washed with 50 mL of 50 mM Tris-HCl (pH 7.6), following which the apoCL-II was eluted with 0.3 M imidazole (Wako Pure Chemical Industries).

(3) Regeneration from ApoCL-II to CL-II Photoprotein

The apoCL-II obtained from the nickel chelate column was suspended in 200 mL of a 50 mM Tris-HCl, 10 mM EDTA, pH 7.6 buffer containing 100 mg of dithiothreitol (DTT, Wako Pure Chemical Industries) as the reducing agent. Chemically synthesized coelenterazine was dissolved in a small amount of methanol, and added to the suspension to a molar concentration 1.2 times the concentration of the apoCL-II eluted in step (2) above. The resulting mixture was held at 4° C. for at least 5 hours, thereby inducing the formation of CL-II photoprotein.

(4) Purification by Ion-Exchange Chromatography Using Q-Sepharose Gel

This solution containing CL-II and apoCL-II was immediately applied to a Q-Sepharose column (Amersham Bioscience; column size, 2.5 cm (dia)×6 cm) equilibrated with a 20 mM Tris-HCl, 10 mM EDTA, pH 7.6 buffer, and the CL-II was thereby desorbed. The column was washed with 20 mM Tris-HCl (pH 7.6), 10 mM EDTA solution until the absorbance at 280 nm of the washings leaving the column fell to 0.05 or below. The CL-II and apoCL-II fractions adsorbed by the column were eluted with 0.15 M NaCl.

(5) Purification of CL-II with Butyl Sepharose 4 Fast Flow Gel

Separation of the CL-II which formed a complex with coelenterazine and the apoCL-II which did not was carried out using Butyl Sepharose 4 Fast Flow Gel (hydrophobic chromatography). The active fraction that eluted from a Q-Sepharose column was adjusted to a final ammonium sulfate concentration of 2 M. Next, the insoluble fraction was removed by centrifugal separation, and the supernatant was recovered. This supernatant was applied to a Butyl Sepharose 4 Fast Flow column (Pharmacia; column size, 2 cm (dia)×8 cm) equilibrated with a 20 mM Tris-HCl, 10 mM EDTA, pH 7.6 buffer containing 2M ammonium sulfate, and was eluted at an ammonium sulfate concentration of 1 M, thereby recovering an orange CL-II fraction having a luminescent activity. The apoCL-II was eluted with the 20 mM Tris-HCl, 10 mM EDTA, pH 7.6 solution alone. The amount of protein was determined from the protein concentration obtained using a commercial kit (BioRad) based on the Bradford assay and using bovine serum albumin (Pierce Biotechnology) as the standard substance.

Figure 4:
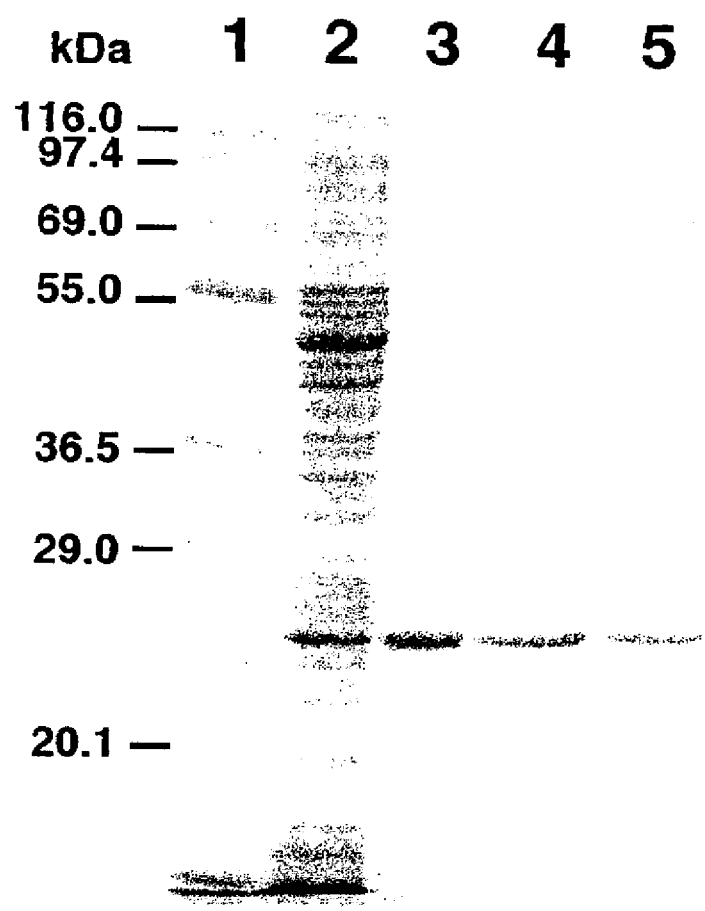
FIG. 4 shows the results of SDS-PAGE analysis at the stage of apoCL-II and CL-II purification. The specimens in the respective lanes were as follows. Lane 1: Protein molecular weight markers (Tefco): β-galactosidase (116,000), phospholipase B (97,400), bovine serum albumin (69,000), glutamate dehydrogenase (55,000), lactate dehydrogenase (36,500), carbonate dehydrogenase (29,000), trypsin inhibitor (20,100); Lane 2: Supernatant (protein, 24 μg) obtained by the centrifugation at 12,300 g of an ultrasonicate of a transformed strain of *Escherichia coli* that expressed recombinant apoCL-II; Lane 3: Fraction eluted from nickel chelate column (protein, 5.4 μg); Lane 4: Fraction eluted with 0.15 M NaCl from Q-Sepharose column (protein, 2.7 μg); Lane 5: Fraction eluted from Butyl Sepharose 4 Fast Flow column (protein, 1.45 μg)

SDS-Page analysis was carried out on each of the purification step fractions under reducing conditions using a 12% (w/v) polyacrylamide gel. As shown in FIG. 4, it is apparent from the results of 12% (w/v) SDS-Page analysis that the final purification fraction had a molecular weight of 25 kDa and a purity of at least 95%. As shown in Table 3, purified CL-II was obtained from 2 liters of the cultured bacteria at an activity recovery ratio of 21.5% and a yield of 13 mg.

Measurement of the luminescence at the stage of CL-II purification was carried out as follows. First, 50 mM Tris-HCl (pH 7.6), 2-mercaptoethanol (1 μl), and the light-emitting substrate coelenterazine dissolved in ethanol (1 μg/μl) were mixed into 1 mL of the reaction solution used for measurement, following which apoCL-II was added and the reaction was carried out on ice (4° C.) for 2 hours. Next, 100 μl of a 50 mM calcium solution was added to 1 μl of the regenerated CL-II photoprotein solution, thereby commencing the light-emitting reaction. The light-emitting activity was measured using a TD-4000 (Labo Science) luminometer, and evaluated based on the maximum value (Imax).

TABLE 3

CL-II Purification Yield

| Step | Total Amount (mL) | Total Protein (mg) | Total Activity ($\times 10^6$ rlu) | Relative Activity ($\times 10^6$/mg) | Recovery (%) Protein | Recovery (%) Activity |
|---|---|---|---|---|---|---|
| Crude extract | 200 | 960 | 73,520 | 160 | 100 | 100 |
| Nickel chelate gel | 200 | 190 | 36,280 | 504 | 19.8 | 49.3 |
| Q-Sepharose gel | 50 | 40 | 28,400 | 710 | 4.2 | 38.6 |
| Butyl Sepharose gel | 13 | 13 | 15,802 | 1,216 | 1.4 | 21.5 |

Reference Example 1

Construction of ApoCL-I Protein Expression Vector

The gene DNA fragment coding for CL-I from the cDNA clone pCL41 obtained in Example 2 was prepared using the PCR method. The CL-I protein expression vector was constructed by inserting this DNA fragment at the restriction enzyme SacI/XhoI site of the expression vector piP-H-M(11) obtained in Example 4. That is, a polymerase chain reaction (cycle conditions: 25 cycles, each consisting of 1 minute at 94° C., 1 minute at 50° C. and 1 minute at 72° C.) was carried out by means of a PCR kit (Nippon Gene) with pCL41 (Inouye, S, and Tsuji, F. I.: FEBS Lett. 315, 343-346 (1993)) as the template and using the PCR primer pair: CLI-N-EL-SacI (5' ggcGAGCTCAGACCCAACTTCGACAAC 3') (SEQ ID NO: 37) and CLI-C-XhoI (5' cggCTCGAGTTAACCAACAAAATTGCCGTA 3') (SEQ ID NO: 38). The resulting fragment was purified with a PCR purification kit (Qiagen) and digested with the restriction enzyme SacI/XhoI, then inserted at the restriction enzyme SacI/XhoI site of piP-H-M (11), thereby constructing the expression vector piP-H-CLI (FIG. 3B). Verification of the insert DNA was carried out by using a DNA sequencer (ABI) to determine the nucleotide sequence.

Reference Example 2

Purification of CL-I

Expression of Recombinant ApoCL-I in *E. coli*

The CL-I gene expression vector piP-H-CL-I obtained in Reference Example 1 was used to express recombinant CL-I in *E. coli*. The vector was inserted into the *E. coli* strain WA802 by a conventional method, and the resulting transformed strain was cultured overnight at 25° C., following which it was inoculated onto 10 mL of LB liquid medium (composed of 10 g of bactotryptone, 5 g of yeast extract and 5 g of sodium chloride per liter of water; pH 7.2) containing ampicillin (50 μg/mL) and additionally cultured at 37° C. for 18 hours. The culture was then added to 5 vessels of 400 mL each of fresh LB liquid medium (total amount, 2 liters) and cultivated at 37° C. for 18 hours. Following cultivation, the bacterial cells were collected by centrifugation (5 minutes at 5,000 rpm), yielding a starting material for CL-I extraction.

(2) apoCL-I Extraction and Purification from Cultured Bacteria

After being harvested, the cultured bacteria were suspended in 200 mL of 50 mM Tris-HCl (pH 7.6), and subjected three times to 2 minutes each of ultrasonic disruption under ice cooling (Branson, Sonifier model cycle 250). The resulting cell ultrasonicate was then centrifuged at 10,000 rpm (12,300×g) and 4° C. for 20 minutes. The resulting soluble fraction was applied to a nickel chelate column (Amersham Bioscience; column size: 1.5 cm (dia)×5 cm), and the apoCL-I was desorbed. The column was then washed with 50 mL of 50 mM Tris-HCl (pH 7.6), following which the apoCL-I was eluted with 0.3 M imidazole (Wako Pure Chemical Industries).

(3) Regeneration from ApoCL-I to CL-I Photoprotein

The apoCL-I obtained from the nickel chelate column was suspended in 200 mL of a 50 mM Tris-HCl, 10 mM EDTA, pH 7.6 buffer containing 100 mg of dithiothreitol (DTT, Wako Pure Chemical Industries) as the reducing agent. Chemically synthesized coelenterazine was dissolved in a small amount of methanol, and added to the suspension to a molar concentration 1.2 times the concentration of the apoCL-I eluted in step (2) above. The resulting mixture was held at 4° C. for at least 5 hours, thereby inducing the formation of CL-I photoprotein.

(4) Purification by Ion-Exchange Chromatography Using Q-Sepharose Gel

This solution containing CL-I and apoCL-I was immediately applied to a Q-Sepharose column (Amersham Bioscience; column size, 2.5 cm (dia)×6 cm) equilibrated with a 20 mM Tris-HCl, 10 mM EDTA, pH 7.6 buffer, and the CL-I was thereby desorbed. The column was washed with 20 mM Tris-HCl (pH 7.6), 10 mM EDTA solution until the absorbance at 280 nm of the washings leaving the column fell to 0.05 or below. The CL-I and apoCL-I fractions adsorbed by the column were eluted with 0.15 M NaCl.

(5) Purification of CL-I with Butyl Sepharose 4 Fast Flow Gel

Separation of the CL-I which formed a complex with coelenterazine and the apoCL-I which did not was carried out using Butyl Sepharose 4 Fast Flow Gel (hydrophobic chromatography). The active fraction that eluted from a Q-Sepharose column was adjusted to a final ammonium sulfate concentration of 2 M. Next, the insoluble fraction was removed by centrifugal separation, and the supernatant was recovered. This supernatant was applied to a Butyl Sepharose 4 Fast Flow column (Pharmacia; column size, 2 cm (dia)×8 cm) equilibrated with a 20 mM Tris-HCl, 10 mM EDTA, pH 7.6 buffer containing 2M ammonium sulfate, and was eluted at an ammonium sulfate concentration of 1 M, thereby recovering an orange CL-I fraction having a luminescent activity. The apoCL-I was eluted with the 20 mM Tris-HCl, 10 mM EDTA, pH 7.6 solution alone. The amount of protein was determined from the protein concentration obtained using a commercial kit (BioRad) based on the Bradford assay and using bovine serum albumin (Pierce Biotechnology) as the standard substance.

Figure 5:
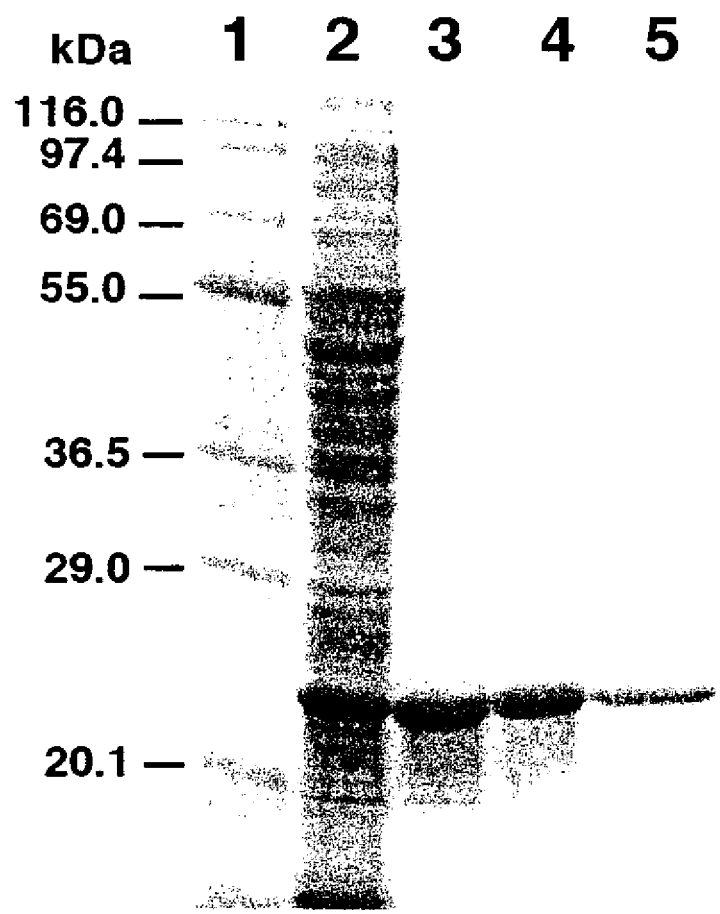
FIG. 5 shows the results of SDS-PAGE analysis at the state of apoCL-I and CL-I purification. The specimens in the respective lanes were as follows. Lane 1: Protein molecular weight markers (Tefco); Lane 2: Supernatant (protein, 29 μg) obtained by the centrifugation at 12,300 g of an ultrasonicate of a transformed strain of *E. coli* that expressed recombinant apoCL-I; Lane 3: Fraction eluted from nickel chelate column (protein, 6.6 μg); Lane 4: Fraction eluted with 0.15 M NaCl from Q-Sepharose column (protein, 5.4 μg); Lane 5: Fraction eluted from Butyl Sepharose 4 Fast Flow column (protein, 2.0 μg)

SDS-Page analysis was carried out on each of the purification step fractions under reducing conditions using a 12% (w/v) polyacrylamide gel. As shown in FIG. 5, a single band corresponding to protein having a molecular weight of 25 kDa was detected and it was apparent that the purity was at least 95%. As shown in Table 4, purified CL-I was obtained from 2 liters of the cultured bacteria at an activity recovery ratio of 32.1% and a yield of 20 mg.

TABLE 4

| | CL-I Purification Yield | | | | | |
|---|---|---|---|---|---|---|
| Step | Total Amount (mL) | Total Protein (mg) | Total Activity (×$10^6$ rlu) | Relative Activity (×$10^6$/mg) | Recovery (%) Protein | Activity |
| Crude extract | 200 | 1340 | 84,800 | 63 | 100 | 100 |
| Nickel chelate gel | 200 | 85.9 | 41,333 | 481 | 6.4 | 48.7 |
| Q-Sepharose gel | 43 | 68.8 | 39,433 | 573 | 5.1 | 46.5 |
| Butyl Sepharose gel | 19 | 20.0 | 27,190 | 1,363 | 1.5 | 32.1 |

Reference Example 3

Preparation of Recombinant Aequorin

Recombinant aequorin was obtained by expressing the recombinant aequorin gene in the *E. coli* strain described in Japanese Patent Application Laid-open No. H1-132397, bonding the product with coelenterazine, and regeneration to recombinant aequorin, followed by purification as described in Japanese Patent Application Laid-open No. 2001-270899. The N-terminal end of the resulting recombinant aequorin was composed of 191 amino acids that started with Ala-Asn-Ser-.

Reference Example 4

Expression of the Photoprotein Obelin

Using the apoobelin expression vector pOPHO (Lux Biotechnology), apoobelin expression was carried out according to the specifications provided. Next, as with the regeneration of other photoproteins, the obelin was regenerated by incubation together with coelenterazine at 4° C. in the presence of 0.1% (v/v) of the reducing agent 2-mercaptoethanol.

Test Example 1

Confirming Cleavage of the Signal Peptide by Mass Spectroscopy

The calcium-bonded photoproteins CL-II and CL-I prepared in Example 6 and Reference Example 2 were measured by matrix-assisted laser desorption time-of-flight mass spectrometry (MALDI-TOF-MS) with an AutoFLEX (Bruker Daltonics). The molecular weight standards used were angiotensin I (m/z, 1296.69), insulin (m/z, 5734.59), apomyoglobin (m/z, 16952.60), and apoaequorin (m/z, 2163.20). Sinapic acid (Invitrogen) was used as the matrix. The measured values obtained were 23188±5 for CL-II and 23166±4 for CL-I. It was apparent from these results that the OmpA signal peptide sequence for secretion had been correctly cleaved.

Test Example 2

Spectroscopic Analysis by Measurement of Absorption/Emission Spectra

Absorption spectra of the purified calcium-bonded photoproteins were measured in a quartz cell having a 10 mm optical path using a spectrophotometer (JASCO V-560). The measurement conditions were as follows: bandpass, 1.0 nm; response, medium; scan rate, 200 nm/minute; 22 to 25° C. Emission spectra were measured in a quartz cell having a 10 mm optical path using a fluorescence spectrophotometer (JASCO FP-6500) with the excitation source turned off. The measurement conditions were as follows: bandpass, 1.5 nm; response, 0.5 second; scan rate, 60 nm/minute; 22 to 25° C. The results obtained using aequorin (AQ) as the control are shown in Table 5.

TABLE 5

Spectral Analysis of Aequorin (AQ), Clytin-I (CL-I) and Clytin-II (CL-II)

| Spectral Analysis | Aequorin (AQ) | Clytin-I (CL-I) | Clytin-II (CL-II) |
|---|---|---|---|
| Absorption Spectra | | | |
| Absorption maximum (nm) | 281, 291, 460 | 283, 291, 460 | 283, 291, 460 |
| Absorption ratio (460 nm/280 nm) | 0.031 | 0.032 | 0.031 |
| Emission Spectra | | | |
| Emission maximum (nm) | 460 | 470 | 470 |
| Full width at half maximum of emission spectrum (nm) | 84 | 76 | 74 |

The absorption value at 460 nm was absorption due to the peroxide of coelenterazine, enabling the concentration of the photoprotein to be determined. Also, the fact that the 460 nm/280 nm ratios in the three different photoprotein absorption spectra were 0.031 to 0.032 indicates that such absorption spectra may be used for assaying the purity of the purified protein.

Test Example 3

Measurement of Emission Patterns for Aequorin, CL-I and CL-II

Emission measurements for comparing emission patterns were carried out using a Centro LB 960 (Berthold Technologies) luminometer. The luminescence reaction was initiated by adding a 100 1 µl of 50 mM calcium solution to 1 µl of a photoprotein solution, light emission was measured for 5 seconds at 0.1 second intervals, and the luminescence activity was plotted.

Figure 6:
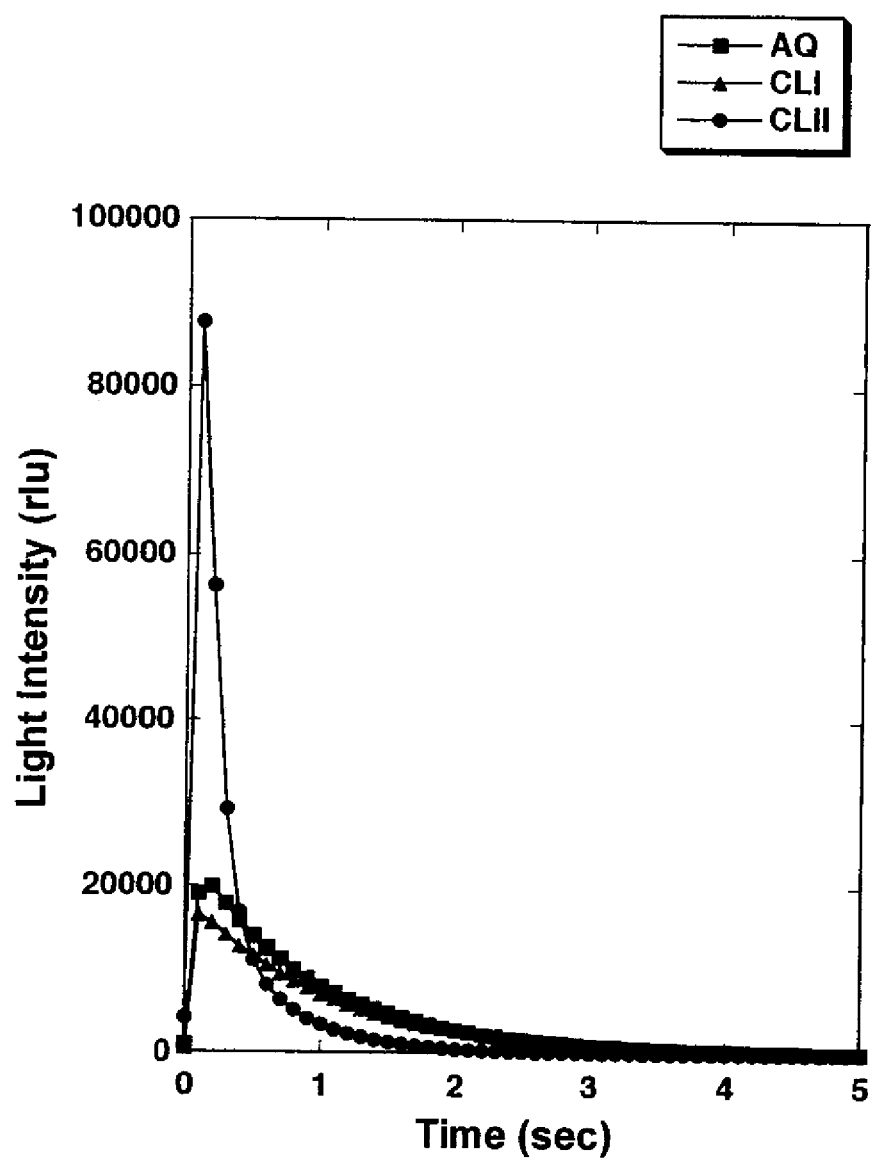
FIG. 6 shows the luminescence patterns obtained for CL-I, CL-II and aequorin with the addition of calcium. Here, "CLI" stands for CL-I, "CLII" stands for CL-II, and "AQ" stands for aequorin.
Figure 7:
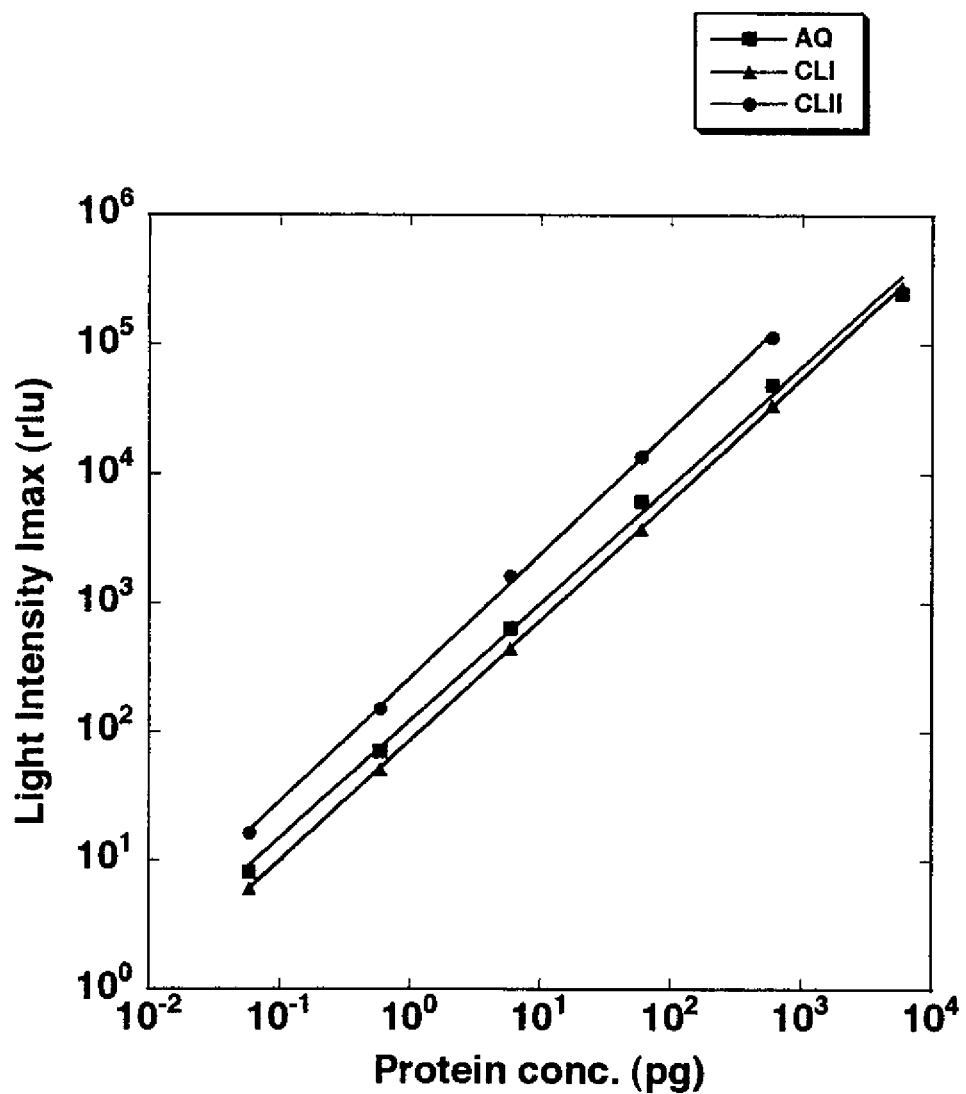
FIG. 7 shows the correlation between the concentrations of CL-I, CL-II and aequorin protein and their maximum luminescence intensities. "CLI" stands for CL-I, "CLII" stands for CL-II, and "AQ" stands for aequorin.

The luminescence patterns for aequorin, CL-I and CL-II are shown in FIG. 6. The S/N ratio for CL-II was clearly better than those for aequorin and CL-I. FIG. 7 shows the correlation between the concentration of photoprotein and the maximum luminescence intensity (Imax) when the concentration of photoprotein was normalized at 460 nm. At the same protein concentration, the maximum luminescence intensity of CL-II was clearly higher than the intensities for aequorin and CL-I. Moreover, CL-II exhibits protein concentration-dependent linearity, confirming that it is capable of being used as an assay probe.

Test Example 4

Comparison of Total Luminescences for Aequorin, CL-I and CL-II

Figure 8:
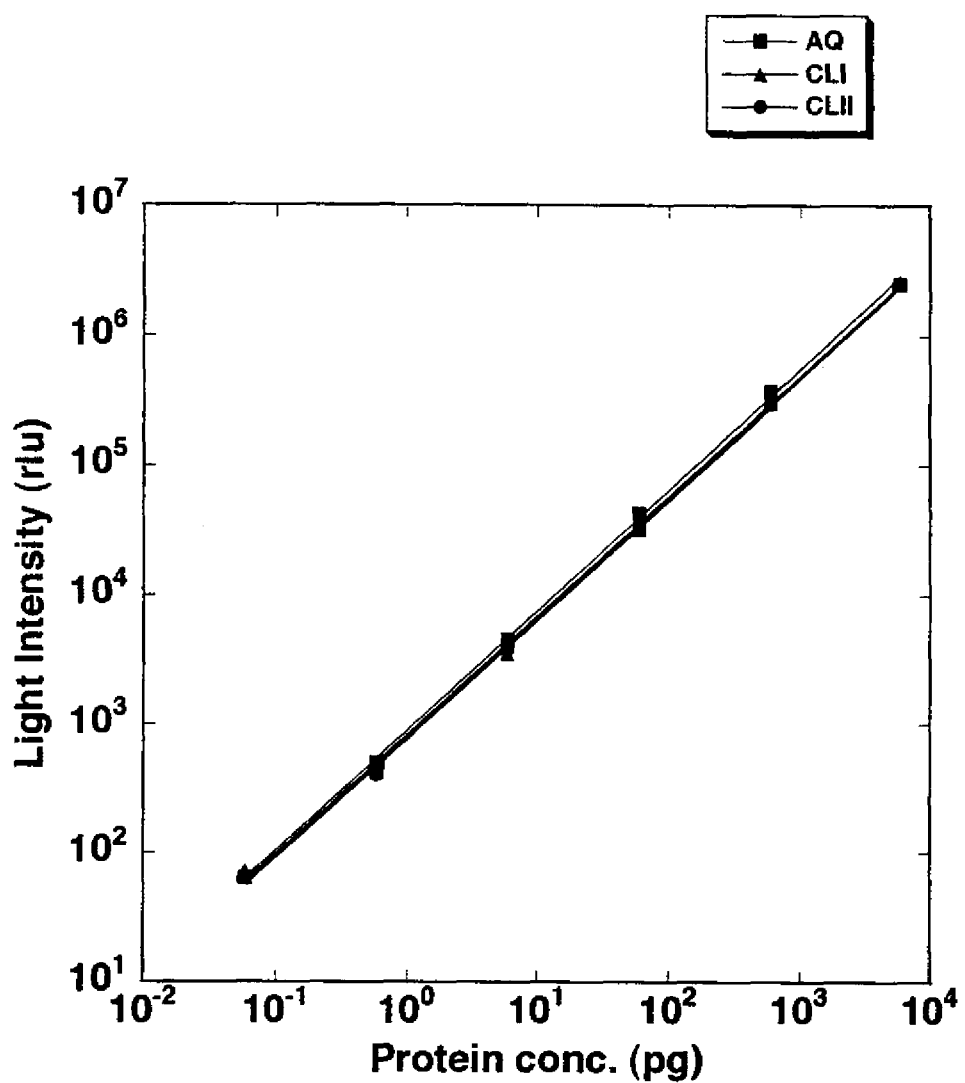
FIG. 8 shows the correlation between the concentrations of CL-I, CL-II and aequorin protein and the total amount of light emitted. "CLI" stands for CL-I, "CLII" stands for CL-II, and "AQ" stands for aequorin.

The total luminescence over a period of 5 seconds for the aequorin, CL-I and CL-II measured in Test Example 3 was determined by integrating the luminescence values obtained at 0.1 second intervals. Those results are shown in FIG. 8. The total luminescence values for the respective photoproteins upon calcium addition were substantially identical at the same protein concentration. From these results and the results of Test Example 3, it is apparent that CL-II can be more sensitively detected than aequorin at the same protein concentrations.

Test Example 5

Half-Lives of Luminescence by Aequorin, CL-I CL-II and Obelin

Figure 9:
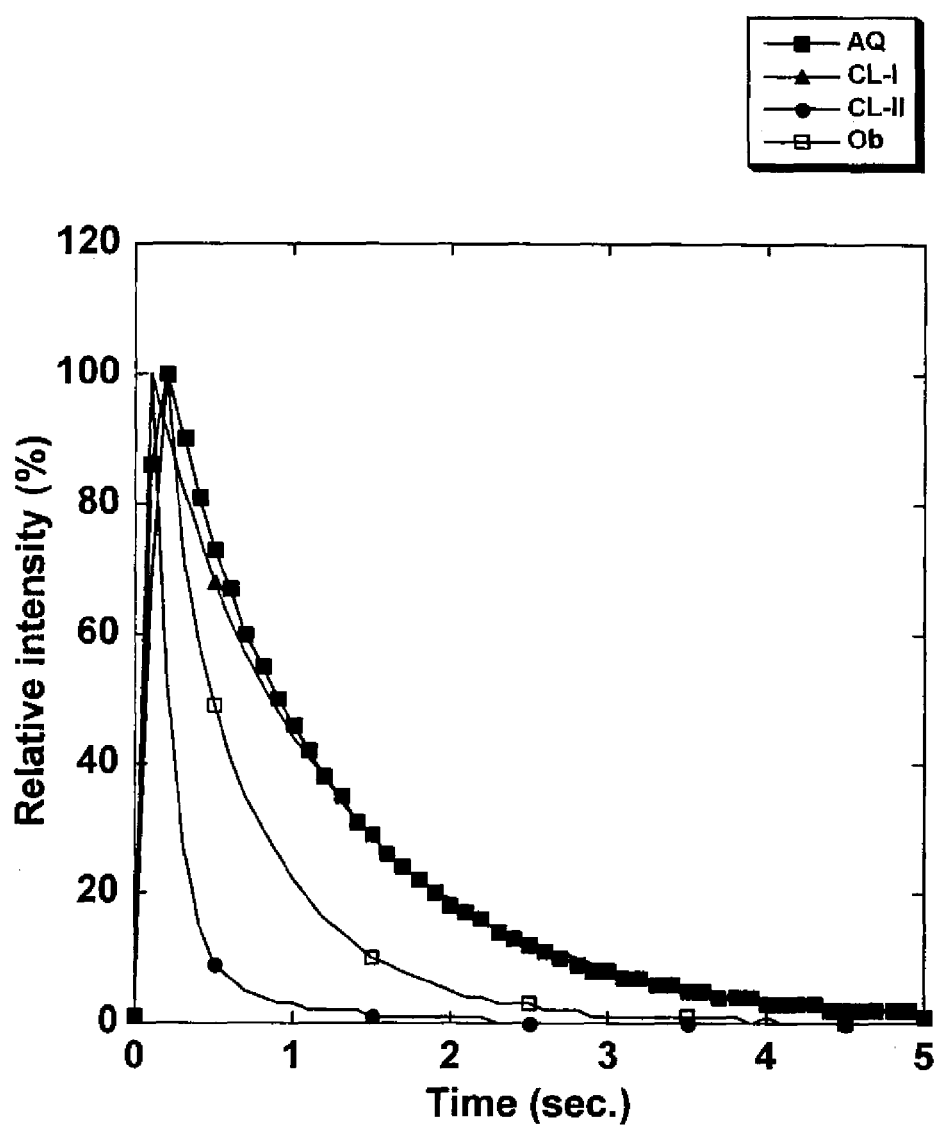
FIG. 9 shows the normalized luminescence pattern images created in the luminescence patterns for CL-I, CL-II, aequorin and obelin. "AQ" stands for aequorin and "Ob" stands for obelin.

Normalized luminescence pattern images were created in the luminescence patterns for CL-I, CL-II, aequorin and obelin (FIG. 9), and the decay times were compared. Those half-lives (the length of time until the value falls to one-half the Imax) and the luminescence rise times are shown in Table 6. When the luminescence has a short half-life, the reactions occur more briefly, exhibiting a better S/N ratio. Hence, CL-II clearly provided the best results.

TABLE 6

Luminescence Half-Lives and Rise Times for Aequorin, CL-I, CL-II and Obelin

| Photoprotein | Half-life of luminescence ($T_{1/2}$, sec) | Rise time of luminescence ($I_{max}$, sec) |
|---|---|---|
| Aequorin | 0.90 | 0.2 |
| CL-I | 0.87 | 0.1 |
| CL-II | 0.20 | 0.1 |
| Obelin | 0.49 | 0.2 |

INDUSTRIAL APPLICABILITY

The proteins of the invention are able to form holoproteins composed of the inventive protein and a peroxide of the light-emitting substrate coelenterazine. The holoproteins of the invention exist in the state of a complex formed from the inventive protein and a peroxide of coelenterazine. When a calcium ion binds to the complex, light is momentarily emitted. This luminescence has a number of excellent properties, including a strong (high) maximum luminescence intensity (Imax) per unit weight of protein, rapid decay of the luminescence, and a good S/N ratio. Accordingly, the proteins of the invention and the holoproteins of the invention may be suitably employed to detect or measure calcium ions. Moreover, the proteins and holoproteins of the invention may be used as reporter proteins to measure the transcription activity of promoters. In addition, the proteins and holoproteins of the invention may also be used as detection markers and as materials for recreational products.

The polynucleotides of the invention code for the above-described protein of the invention, and thus may be used as a reporter gene.

Moreover, the polynucleotides of the invention, the vectors of the invention and the transformants of the invention may be used in the production of the inventive proteins.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

The invention claimed is:

1. A method for detecting calcium ions in a solution, comprising the following steps;
  Step (1): providing a holoprotein comprising a peroxide of coelenterazine or a peroxide of a coelenterazine derivative and an apoprotein comprising a peptide sequence selected from the group consisting of SEQ ID NO: 1, SEQ ID NO: 3, SEQ ID NO: 5, SEQ ID NO: 7, SEQ ID NO: 9 and SEQ ID NO: 11;
  Step (2): contact said holoprotein with a solution suspected of having calcium ions and
  Step (3): determine the luminescence of the holoprotein: calcium complex;
  wherein the luminescence correlates with the amount of calcium ions in solution.

2. The method according to claim 1, wherein said apoprotein further comprises at least one of a peptide sequence for purification and a secretory signal peptide sequence.

3. A method for measuring changes in intracellular calcium concentration in response to an external stimuli, said method comprising:
  Step (1): providing a host cell that expresses an apoprotein comprising at least one of items (a) and (b):
    wherein (a) is a polypeptide comprising the peptide sequence selected from the group consisting of SEQ ID NO: 1, SEQ ID NO: 3, SEQ ID NO: 5, SEQ ID NO: 7, SEQ ID NO: 9 and SEQ ID NO: 11, and
    wherein (b) is a polypeptide comprising the peptide sequence selected from the group consisting of SEQ ID NO: 1, SEQ ID NO: 3, SEQ ID NO: 5, SEQ ID NO: 7, SEQ ID NO: 9 and SEQ ID NO: 11, and which has the ability to bond with at least one peroxide selected from the group consisting of a peroxide of coelenterazine and a peroxide of a coelenterazine derivative;
  Step (2): providing a peroxide of coelenterazine or a peroxide of a coelenterazine derivative to said host cell to form an intracellular holoprotein comprising the apoprotein and peroxide of coelenterazine and a peroxide of a coelenterazine derivative;
  Step (3): providing an external stimuli to said host cell;
  Step (4): determine the luminescence of the holoprotein: calcium complex;
  wherein the luminescence correlates with the ability of the external stimuli to increase or decrease intracellular calcium concentration.

4. A method for determining the transcriptional activation of a promoter by a candidate compound, said method comprising:
  Step (1): providing a vector comprising a target promoter operatively linked to a polynucleotide encoding a reporter apoprotein comprising at least one of items (a) and (b),wherein:
    (a) is a polypeptide comprising the peptide sequence selected from the group consisting of SEQ ID NO: 1, SEQ ID NO: 3, SEQ ID NO: 5, SEQ ID NO: 7, SEQ ID NO: 9 and SEQ ID NO: 11, and
    wherein (b) is a polypeptide comprising the peptide sequence selected from the group consisting of SEQ ID NO: 1, SEQ ID NO: 3, SEQ ID NO: 5, SEQ ID NO: 7, SEQ ID NO: 9 and SEQ ID NO: 11, and which has the ability to bond with at least one peroxide selected from the group consisting of a peroxide of coelenterazine and a peroxide of a coelenterazine derivative;
  Step (2): transforming a host cell with said vector;
  Step (3): culturing said host cell under conditions which allow the expression of the apoprotein;
  Step (4): contacting the host cell with a candidate compound;

Step (5): isolating or extracting the apoprotein from the host cell or culture broth;

Step (6): contacting the isolated or extracted apoprotein with at least one peroxide selected from the group consisting of a peroxide of coelenterazine and a peroxide of a coelenterazine derivative to form a holoprotein;

Step (7): contact the holoprotein with calcium;

Step (8): determine the luminescence of the holoprotein: calcium complex; wherein the luminescence correlates with the ability of the candidate compound to activate said promoter.

5. The method according to claim 4, wherein said polynucleotide is at least one of items (a) and (b):

wherein (a) is a polynucleotide comprising the nucleotide sequence selected from the group consisting of a nucleotide sequence of SEQ ID NO: 2, SEQ ID NO: 4, SEQ ID NO: 6, SEQ ID NO: 8, SEQ ID NO: 10 and SEQ ID NO: 12, and wherein (b) is a polynucleotide comprising the nucleotide sequence selected from the group consisting of a nucleotide sequence of SEQ ID NO: 2, SEQ ID NO: 4, SEQ ID NO: 6, SEQ ID NO: 8, SEQ ID NO: 10 and SEQ ID NO: 12, and encoding a protein having the ability to bond with at least one peroxide selected from the group consisting of a peroxide of coelenterazine and a peroxide of a coelenterazine derivative so as to form a holoprotein that emits light under the action of a calcium ion.

* * * * *